(12) United States Patent
Roh et al.

(10) Patent No.: US 12,213,741 B2
(45) Date of Patent: *Feb. 4, 2025

(54) APPARATUS FOR ROBOTIC JOINT ARTHROSCOPIC SURGERY

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US); Mihir Patel, Carmel, IN (US)

(73) Assignee: IX Innovation LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/461,723

(22) Filed: Sep. 6, 2023

(65) Prior Publication Data

US 2024/0138922 A1     May 2, 2024

Related U.S. Application Data

(63) Continuation of application No. 17/974,509, filed on Oct. 26, 2022, now Pat. No. 11,786,313.

(51) Int. Cl.
| | |
|---|---|
| *A61B 34/10* | (2016.01) |
| *A61B 34/00* | (2016.01) |
| *A61B 34/30* | (2016.01) |
| *A61B 34/35* | (2016.01) |

(Continued)

(52) U.S. Cl.
CPC .............. *A61B 34/10* (2016.02); *A61B 34/25* (2016.02); *A61B 34/35* (2016.02); *A61B 2034/105* (2016.02); *A61B 2034/252* (2016.02); *A61B 2034/256* (2016.02); *A61B 2034/305* (2016.02);

(Continued)

(58) Field of Classification Search
CPC ......... A61B 34/10; A61B 34/25; A61B 34/35; A61B 2034/105; A61B 2034/252; A61B 2034/256; A61B 2034/305; A61B 2090/374; A61B 2090/376; A61B 90/361; A61B 90/96; A61B 90/98; A61B 2034/104; A61B 34/20; A61B 2090/3937;

(Continued)

(56) References Cited

U.S. PATENT DOCUMENTS

| | | | |
|---|---|---|---|
| 11,350,995 B2* | 6/2022 | Finley | A61B 34/25 |
| 11,464,573 B1* | 10/2022 | Roh | A61B 34/10 |
| 2022/0160430 A1* | 5/2022 | Landon | G16H 40/67 |

(Continued)

*Primary Examiner* — Harry Y Oh
(74) *Attorney, Agent, or Firm* — Perkins Coie LLP

(57) ABSTRACT

Methods, apparatuses, and systems for performing robotic joint arthroscopic surgery are disclosed. The disclosed systems use a surgical robot to perform robotic joint arthroscopic surgery for soft tissue. The disclosed systems enable a surgeon or physician to perform a virtual surgical procedure in a virtual environment, storing robotic movements, workflow objects, user inputs, or a description of tools used. The surgical robot filters the stored data to determine a surgical workflow from the stored data. The surgical robot displays information describing a surgical step in the surgical workflow, enabling the surgeon or physician to optionally adjust the surgical workflow. The surgical robot stores the optional adjustments and performs the surgical procedure on a patient by executing surgical actions of the surgical workflow.

9 Claims, 20 Drawing Sheets

(51) Int. Cl.
*A61B 90/00* (2016.01)
*A61F 2/30* (2006.01)
(52) U.S. Cl.
CPC ... *A61B 2090/374* (2016.02); *A61B 2090/376* (2016.02); *A61F 2002/30952* (2013.01)
(58) Field of Classification Search
CPC .................. A61B 34/30; A61B 34/32; A61F 2002/30952; A61F 2002/4632; A61F 2002/4633
See application file for complete search history.

(56) References Cited

U.S. PATENT DOCUMENTS

| | | | |
|---|---|---|---|
| 2022/0387110 A1* | 12/2022 | Chaoui | G16H 50/20 |
| 2023/0105822 A1 | 4/2023 | Miles et al. | |
| 2023/0107003 A1 | 4/2023 | Roh et al. | |
| 2023/0149114 A1* | 5/2023 | Boese | A61B 34/10 |
| | | | 382/128 |

* cited by examiner

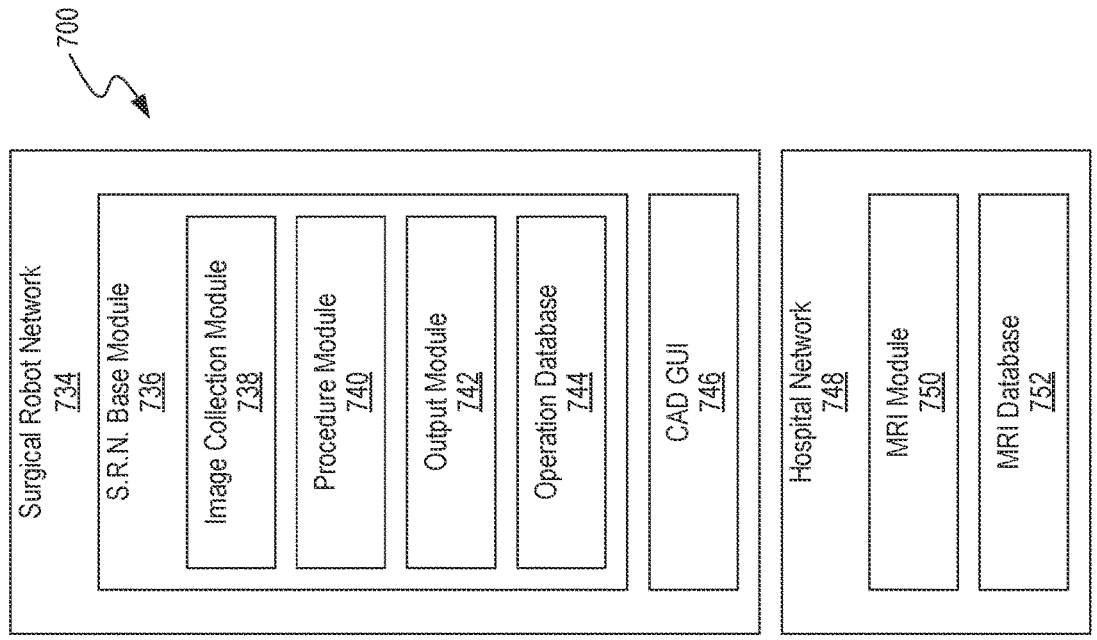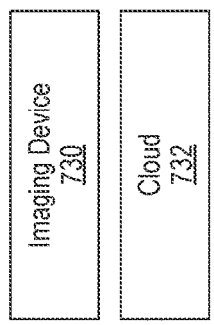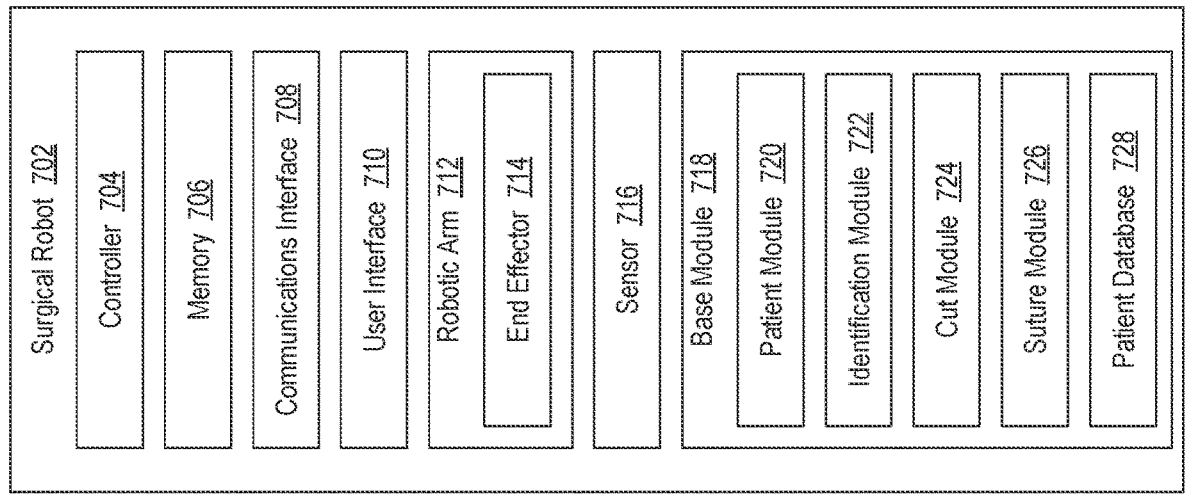
FIG. 7

| Patient ID | Surgery | 3D Image | Phase | Process | Data File |
|---|---|---|---|---|---|
| JS123 | Extensor Digitorum Longus Tendon Repair Surgery | JS123Ankle3D.data | Identification | Identify lacerated tendon | JSID#1.data |
| | | | | 1st end effector secures first side of lacerated tendon | JSID#2.data |
| | | | | 2nd end effector secures second side of lacerated tendon | JSID#3.data |
| | | | Cutting | 3rd end effector secures first side of lacerated tendon | JSCUT#1.data |
| | | | | knife end effector cuts frayed end of the first side of lacerated tendon | JSCUT#2.data |
| | | | | knife end effector is removed | JSCUT#3.data |
| | | | | 3rd end effector releases first side of lacerated tendon | JSCUT#4.data |
| | | | | 3rd end effector secures second side of lacerated tendon | JSCUT#5.data |
| | | | | knife end effector cuts frayed end of the second side of lacerated tendon | JSCUT#6.data |
| | | | | knife end effector is removed | JSCUT#7.data |
| | | | | 3rd end effector releases second side of lacerated tendon | JSCUT#8.data |
| | | | Suture | suture end effector inserts suture intertendinous on fibula side through lacerated portion of tendon | JSSUT#1.data |
| | | | | suture end effector exits suture through dorsal surface of tendon on fibula side | JSSUT#2.data |
| | | | | pass suture ventrally the tendon | JSSUT#3.data |
| | | | | suture end effector inserts suture through dorsal aspect of the tendon on tibia side | JSSUT#4.data |
| | | | | suture end effector exits suture through lacerated region of tendon on tibia side | JSSUT#5.data |

*FIG. 13*

| Patient ID | Surgery | 3D Image | Phase | Process | Data File |
|---|---|---|---|---|---|
| JS123 | Extensor Digitorum Longus Tendon Repair Surgery | JS123Ankle3D.data | Identification | Identify lacerated tendon | JSID#1.data |
| | | | | 1st end effector secures first side of lacerated tendon | JSID#2.data |
| | | | | 2nd end effector secures second side of lacerated tendon | JSID#3.data |
| | | | Cutting | 3rd end effector secures first side of lacerated tendon | JSCUT#1.data |
| | | | | knife end effector cuts frayed end of the first side of lacerated tendon | JSCUT#2.data |
| | | | | knife end effector is removed | JSCUT#3.data |
| | | | | 3rd end effector releases first side of lacerated tendon | JSCUT#4.data |
| | | | | 3rd end effector secures second side of lacerated tendon | JSCUT#5.data |
| | | | | knife end effector cuts frayed end of the second side of lacerated tendon | JSCUT#6.data |
| | | | | knife end effector is removed | JSCUT#7.data |
| | | | | 3rd end effector releases second side of lacerated tendon | JSCUT#8.data |
| | | | Suture | suture end effector inserts suture intertendinous on fibula side through lacerated portion of tendon | JSSUT#1.data |
| | | | | suture end effector exits suture through dorsal surface of the tendon on fibula side | JSSUT#2.data |
| | | | | pass suture ventrally the tendon | JSSUT#3.data |
| | | | | suture end effector inserts suture through dorsal aspect of the tendon on tibia side | JSSUT#4.data |
| | | | | suture end effector exits suture through lacerated region of tendon on tibia side | JSSUT#5.data |

*FIG. 18*

| Patient ID | First Name | Last Name | Area | Data File |
|---|---|---|---|---|
| JS123 | John | Smith | Ankle | JS-Ankle#1.JPEG |
| JS123 | John | Smith | Ankle | JS-Ankle#2.JPEG |
| JS123 | John | Smith | Ankle | JS-Ankle#3.JPEG |
| JS123 | John | Smith | Ankle | JS-Ankle#4.JPEG |
| JS123 | John | Smith | Ankle | JS-Ankle#5.JPEG |
| JS123 | John | Smith | Ankle | JS-Ankle#6.JPEG |
| -- | -- | -- | -- | -- |
| -- | -- | -- | -- | -- |
| -- | -- | -- | -- | -- |

APPARATUS FOR ROBOTIC JOINT ARTHROSCOPIC SURGERY

CROSS-REFERENCE TO RELATED APPLICATION

The application is a continuation of U.S. patent application Ser. No. 17/974,509, filed Oct. 26, 2022, which is incorporated herein by reference in its entirety.

TECHNICAL FIELD

The present disclosure is generally related to automated and robotic surgical procedures and specifically to apparatuses for performing robotic joint arthroscopic surgery.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure, as well as technical surgical errors during the operation. For example, adverse events can occur due to (i) a breakdown in communication within and among the surgical team, care providers, patients, and their families; (ii) delays in diagnosis or failure to diagnose; and (iii) delays in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 7 is a block diagram illustrating an example surgical system, in accordance with one or more embodiments.

FIG. 13 is a chart illustrating an example database, in accordance with one or more embodiments.

FIG. 18 is a chart illustrating an example database, in accordance with one or more embodiments.

DETAILED DESCRIPTION

Figure 1:
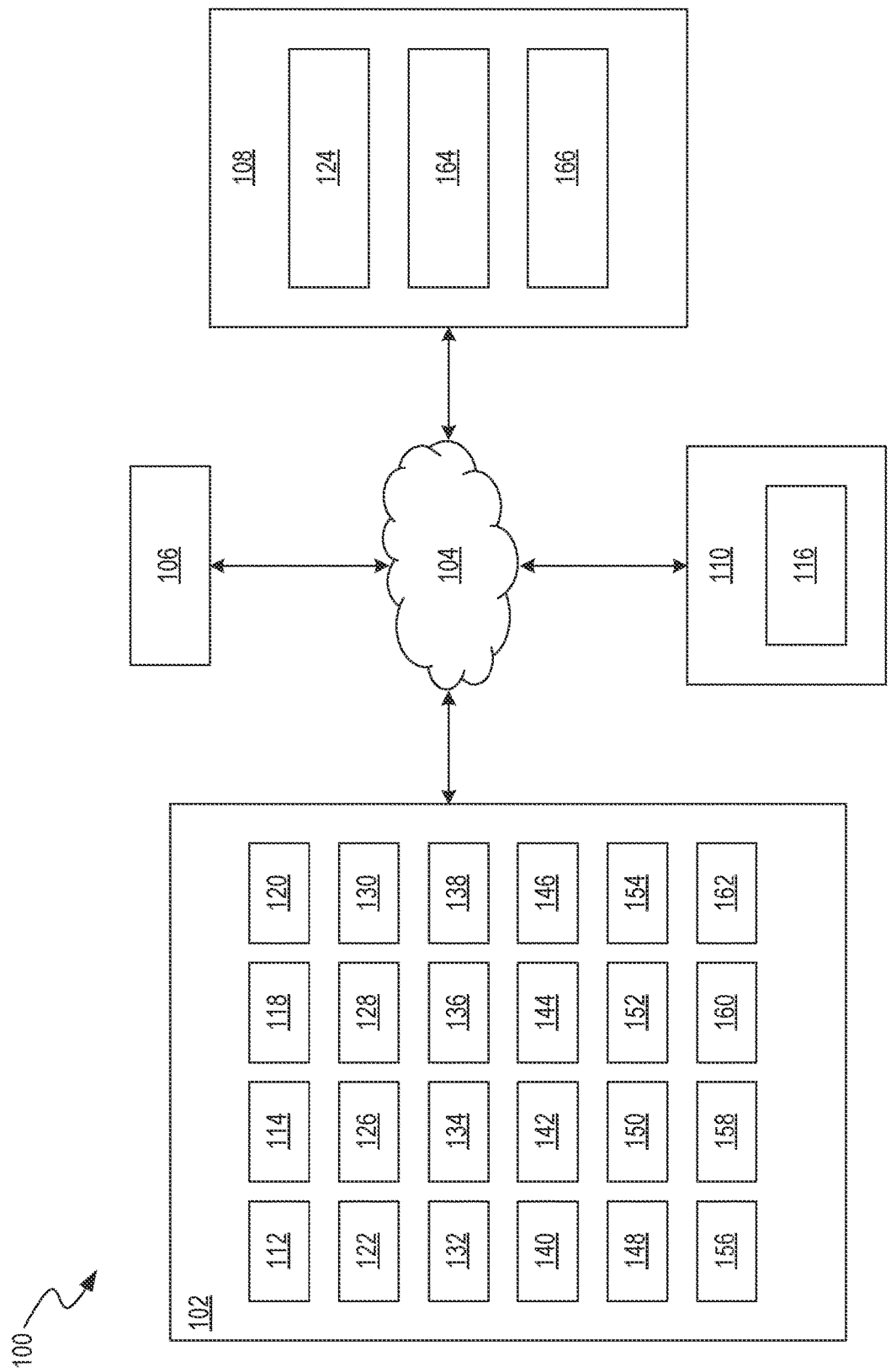
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610a") described as a single instance. Further, plural instances (e.g., "610") refer collectively to a set of components, operations, or structures (e.g., "610a") described as a single instance. The description of a single component (e.g., "610a") applies equally to a like-numbered component (e.g., "610b") unless indicated otherwise. These and other aspects, features, and implementations can be expressed as methods, apparatuses, systems, components, program products, means or steps for performing a function, and in other ways. These and other aspects, features, and implementations will become apparent from the following descriptions, including the claims.

In embodiments, medical imaging is performed using different wavelengths of electromagnetic energy, ultrasounds, magnetic resonance, etc. The different wavelengths when directed towards a subject, such as bone tissue, soft tissue, or any other subject or substance, image different types of tissues with varying depths of penetration. For example, when visible light of a predefined wavelength is directed at bone tissue, a part of the incident light can be absorbed by the bone tissue. As a result, the intensity of the reflected/refracted light is less than that of the incident light. The decrease in the intensity of the incident light can be measured and used to generate an image. In embodiments, different medical devices having capabilities including, but not limited to, X-ray imaging, magnetic resonance imaging (MRI), ultrasound, angiography, or computed tomography (CT) are used. In embodiments, omni-tomographic imaging or grand fusion imaging, such as large-scale fusion of simultaneous data acquisition from multiple imaging modalities (e.g., CT, MRI, positron emission tomography (PET), SPECT, USG, or optical imaging), is used. Composite images, including image data from multiple modalities, are sometimes referred to as "multi-modality images" or "multiple-modality images" herein.

Arthroscopy (also called arthroscopic or keyhole surgery) is a minimally invasive surgical procedure performed on a joint in which an examination and sometimes treatment of damage is performed using an arthroscope, which is an endoscope that is inserted into the joint through a small incision. For example, arthroscopic procedures can be performed during anterior cruciate ligament (ACL) reconstruction. The surgical instruments used by the embodiments disclosed herein are smaller than traditional instruments. A surgeon can view the joint area on a video monitor, and can direct a robot to diagnose or repair torn joint tissue, such as ligaments. The arthroscopic embodiments disclosed herein can be used for the knee, shoulder, elbow, wrist, ankle, foot, and hip.

The embodiments disclosed herein describe methods, apparatuses, and systems for performing robotic joint arthroscopic surgery. The disclosed systems use a surgical robot to perform robotic joint arthroscopic surgery to address soft tissue (e.g., ligament, meniscus, labrum, cartilage, joint surface, or the lateral extensor digitorum longus (EDL) tendon portion of the anatomy). The disclosed systems enable a surgeon or physician to perform a virtual surgical procedure in a virtual environment, storing robotic movements, workflow objects, user inputs, or a description of tools used. The surgical robot filters the stored data to determine a surgical workflow from the stored data. The surgical robot displays information describing a surgical step in the surgical workflow, enabling the surgeon or physician to optionally adjust the surgical workflow. The surgical robot stores the optional adjustments and performs the surgical procedure on a patient by executing surgical actions of the surgical workflow.

In embodiments, the disclosed systems use a surgical robot network that receives medical images of a patient and generates a three-dimensional (3D) rendering of the various medical images. A surgeon or physician is enabled to select workflow objects (such as various tools). The workflow objects can be selected in a sequence for performing actions on the 3D rendering. Data related to the workflow objects and actions in relation to the 3D rendering are stored. The surgeon or physician is enabled to select and perform various threading techniques and input calculations of the actions performed. The user inputs, workflow objects, and actions with respect to the 3D rendering are sent to a surgical robot for performing robotic joint arthroscopic surgery.

In embodiments, a robotic surgical system uses machine learning (ML) to provide recommendations and methods for automated robotic ankle arthroscopic surgery. Historical patient data is filtered to match particular parameters of a patient. The parameters are correlated to the patient. A robotic surgical system or a surgeon reviews the historical patient data to select or adjust the historical patient data to generate a surgical workflow for a surgical robot for performing the robotic arthroscopic surgery.

In some embodiments, a surgical robot receives user inputs, workflow objects, and data files containing surgical actions for robotic movements from a surgery network. Information describing surgical tools required for performing the robotic arthroscopic surgery are displayed on a user interface for the surgical tools to be enabled or disabled. Information describing the robotic arthroscopic surgical steps are displayed on the user interface in a sequence to enable execution of the data files containing the robotic movements. The robotic movements are used to perform surgical steps or assist a surgeon in performing surgical steps.

In some embodiments, a computer-implemented method for performing a robotic arthroscopic surgical procedure includes extracting computer instructions to be executed by a surgical robot from a surgical database. The computer instructions are for performing the robotic arthroscopic surgical procedure. Images of an anatomy of a patient are obtained using an imaging sensor of the surgical robot for performing the robotic arthroscopic surgical procedure based on the computer instructions. Soft tissue (e.g., tendon, ligament, meniscus, labrum, cartilage, or joint surface) of the patient is identified within the anatomy using the images. The methods address soft tissue injury (e.g., laceration, contusion, bruise, sprain, tendonitis, bursitis, stress injuries, or strain). The robotic arthroscopic surgical procedure is for repairing the injury.

The surgical robot performs the robotic arthroscopic surgical procedure based on the computer instructions. One or more end effectors of the surgical robot secure a first location of the soft tissue (e.g., tendon, ligament, meniscus, labrum, cartilage, or joint surface). The one or more end effectors secure a second location of the soft tissue (e.g., tendon, ligament, meniscus, labrum, cartilage, or joint surface). For example, a surgical knife coupled to the one or more end effectors cuts lacerated ends of a tendon to remove frayed material from the lacerated ends. The one or more end effectors suture the lacerated ends to repair the tendon.

In some embodiments, the disclosed systems can perform an arthroscopic surgical procedure on a joint of a patient. The system can acquire data (e.g., user input, patient data, etc.) from user interfaces and storage devices. A ML algorithm can analyze the patient data to determine one or more ligament-attachment joint stabilization steps for the joint. The system can generate a robotic-enabled surgical plan for the joint based on the user input and the one or more ligament-attachment joint stabilization steps. In some implementations, the robotic-enabled surgical plan includes a sequence of surgical steps with corresponding surgical tools for attaching one or more connectors to at least one ligament of the joint and another structure of the patient to promote stabilization of the joint. A GUI can display the robotic-enabled surgical plan for intraoperative viewing by a user (e.g., healthcare provider) while the robotic surgical system robotically operates on the patient. The system can receive, from the user, intraoperative user input associated with one or more of the surgical steps of the robotic-enabled surgical plan. The system determines information to be displayed, via the GUI, based on the received intraoperative user input while controlling one or more of the tools operated by the robotic surgical system according to a selection.

The advantages and benefits of the methods, systems, and apparatuses disclosed herein include compatibility with best practice guidelines for performing surgery in an operating room, e.g., from regulatory bodies and professional standards organizations such as the Association for Surgical Technologists. The imaging systems disclosed use computer networks, the Internet, intranets, and supporting technologies to implement a cost-effective technology to collect, transmit, store, analyze, and use imaging information in electronic formats. As a result, surgical robots can use the embodiments to collect and analyze vast amounts of information, resulting in early diagnoses. The disclosed methods reduce the amount of noise and increase the resolution, replicability, efficiency, and accuracy in collecting and analyzing information. Further, the embodiments disclosed herein enable meta-analyses for more-elaborate diagnostic procedures and reduce the need for repetitive invasive diagnostic testing. In addition, the disclosed systems enable continuous monitoring and analysis of the health of the patient in order to provide real-time assistance to a surgical robot or surgeon during a surgical procedure.

The technologies disclosed provide benefits over traditional open surgery in that a joint does not have to be opened up fully. For knee arthroscopy using the robotic methods disclosed, only two small incisions are made, one for the arthroscope and one for the surgical instruments to be used in the knee cavity. The embodiments reduce recovery time and can increase the rate of success due to less trauma to the connective tissue. The robotic apparatus disclosed results in shorter recovery times with less scarring, because of the smaller incisions. The disclosed methods for robotic surgery use historical data from surgical robots to generate more precise recommendations for patients compared to traditional methods. The disclosed surgical apparatuses perform an ML system using historical data from surgical robots to generate the recommendations. The disclosed systems provide workflows for a surgeon or physician to review and adjust surgical procedures based on historical patient data to generate surgical procedures for patients using an interactive user interface. The embodiments disclosed herein thus provide improved ankle surgery compared to conventional surgery.

Moreover, the disclosed apparatuses provide computer-aided design (CAD) ability to surgeons and physicians to enable them to manipulate a 3D rendering of a region of a patient's anatomy to virtually perform surgery. The disclosed methods provide a workflow process based on CAD software to improve chances of success of detailed steps of a surgical procedure. The disclosed systems enable surgeons to perform virtual surgeries using a robotic system to generate optimal results for a patient, especially for robotic joint arthroscopic surgery for the lateral EDL tendon area of the anatomy. Further, the robotic joint repair surgery technologies disclosed benefit ligament and tendon repair surgery. The surgical robot disclosed performs skillful removal of tissues, precise placement of sutures and bone anchors, and delicate tensioning of the sutures.

Further, the embodiments provide automated and more efficient systems for using multiple imaging modalities, especially those using different wavelengths of electromagnetic waves. Quicker diagnosis of patients is achieved compared to traditional methods via simultaneous or sequential imaging. The automated methods of aligning images taken using different imaging modalities disclosed provided improved analysis of the images to identify medical conditions. In addition, the advantages of the convolutional neural network (CNN) used for ML in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or an outpatient surgery center.

In some embodiments, the system 100 includes one or more medical or surgical patient monitors 112. The monitors 112 can include a vital signs monitor (a medical diagnostic instrument), which can be a portable, battery-powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the body part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end-tidal CO2 monitor or capnography monitor used for measurement of the level of carbon dioxide that is released at the end of an exhaled breath (referred to as end-tidal carbon dioxide, ETCO2). An end-tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal CO2 monitor can be configured as side stream (diverting) or mainstream (non-diverting). A diverting end-tidal CO2 monitor transports a portion of a patient's respired gases from the sampling site to the end-tidal CO2 monitor, while a non-diverting end-tidal CO2 monitor does not transport gas away. Also, measurement by the end-tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in an artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as the bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuro-monitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality (AR) device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably two-dimensional (2D) or three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Two-dimensional (2D) or three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument 130 can consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, MRI, ultrasound, endoscopy, elastography, tactile imaging, thermography, medical photography, and nuclear medicine, e.g., PET. Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used are brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses CT imaging that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where it is working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The SCD 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. A CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR is a digital version of patients' paper charts. The EHR database 106 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

In embodiments, the system 100 uses quantum computing. Quantum computing refers to the use of a computational device or method that uses properties of quantum states defined by quantum mechanics such as superposition, entanglement, etc., to perform computations. Quantum devices use qubits, which are the quantum equivalent of bits in a classical computing system. Qubits have at least two quantum states or probable outcomes. These outcomes, combined with a coefficient representing the probability of each outcome, describes the possible states, or bits of data, which can be represented by the qubits according to the principle of quantum superposition. These states can be manipulated to shift the probability of each outcome, or additionally, add additional possible outcomes to perform computations, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows the greatest promise for drug discovery and simulating the interaction of drugs with biologic systems, however the same technology can also be used to predict the interaction of a biologic system with an implanted device, preventing rejection of an implant by a patient's body. Quantum computing can be used to investigate long term functioning of an implant. Further, quantum computing can be used to study the reaction of a patient to a surgical procedure, during a simulation, before a procedure, or actively during a procedure.

Figure 2:
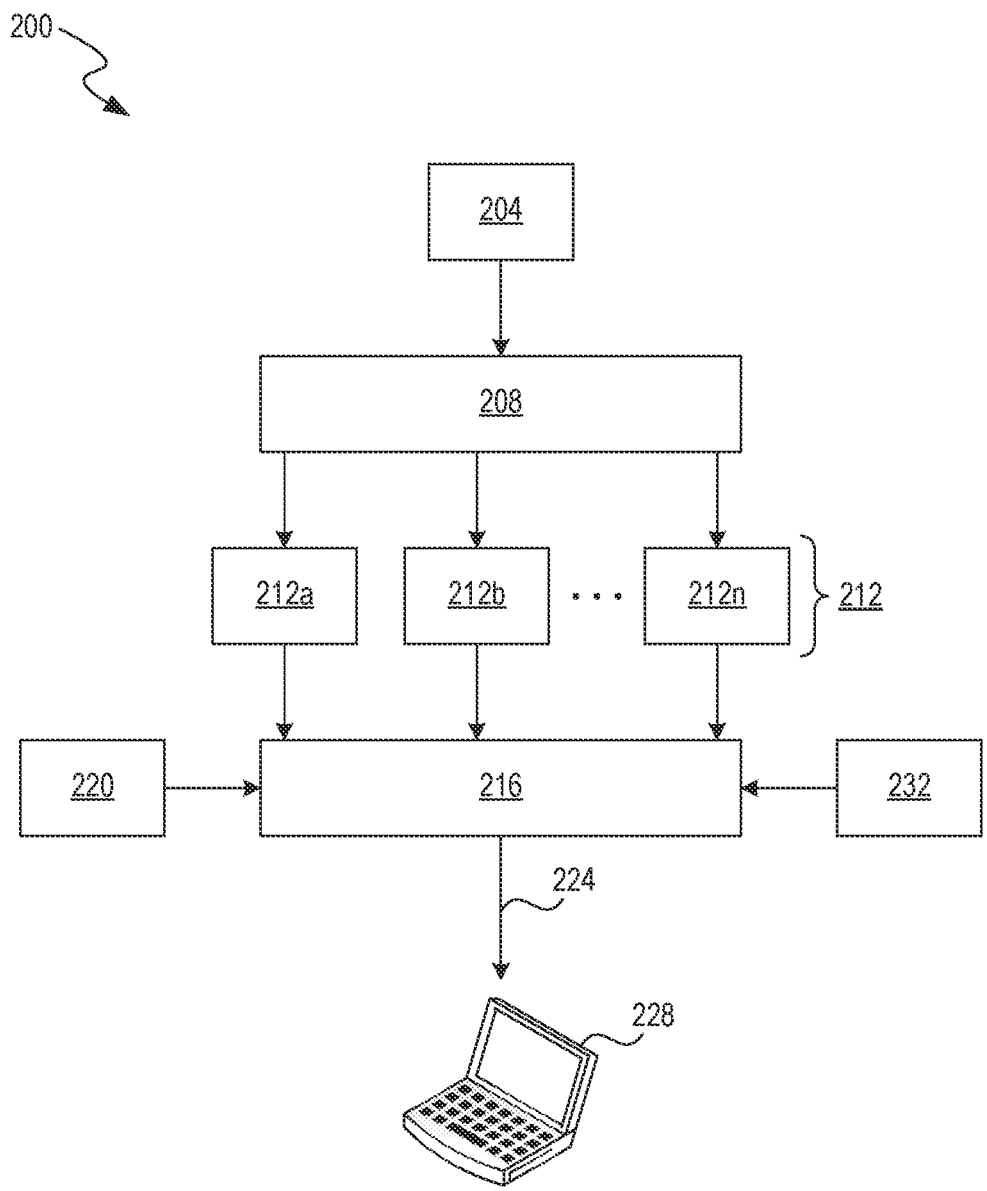
FIG. 2 is a block diagram illustrating an example machine learning (ML) system, in accordance with one or more embodiments.

FIG. 2 is a block diagram illustrating an example ML system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place. The validation set 232 can include data corresponding to confirmed anatomical features, tissue states, tissue conditions, diagnoses, or combinations thereof. This allows the detected values to be validated using the validation set 232. The validation set 232 can be generated based on analysis to be performed.

Figure 3:
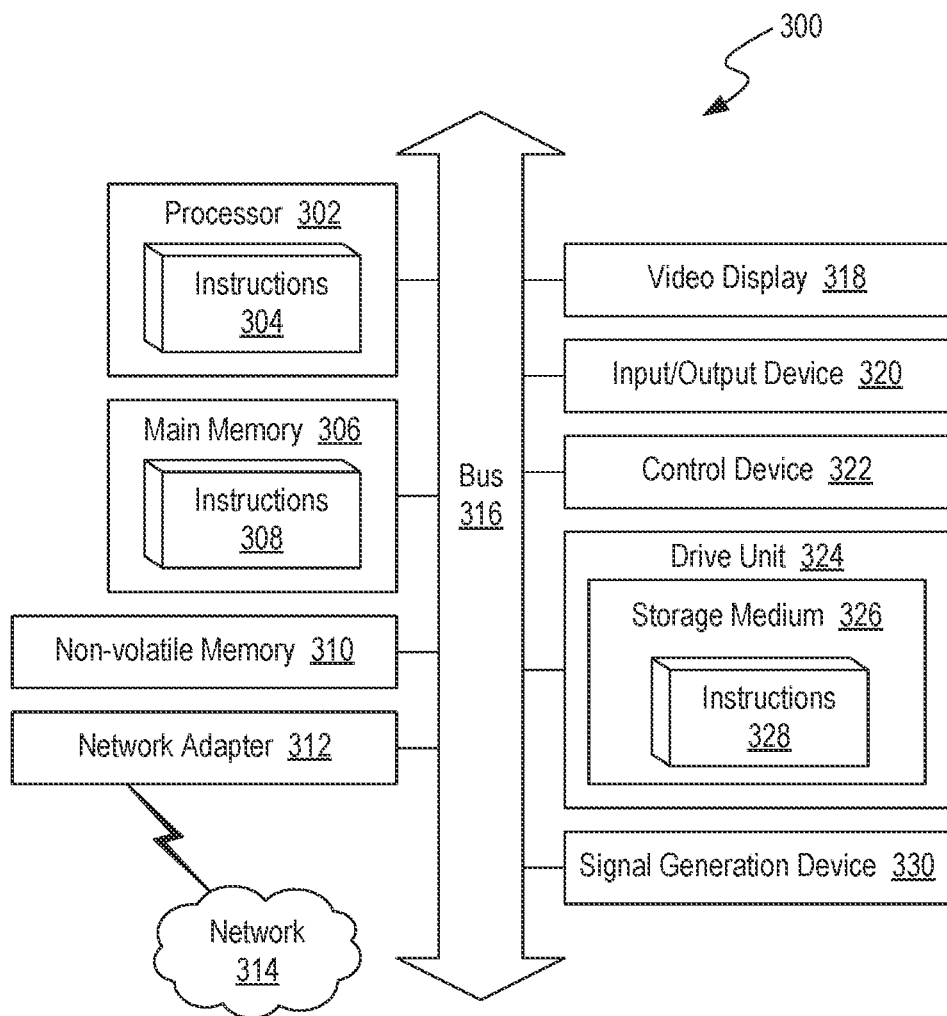
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual reality (VR)/AR systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
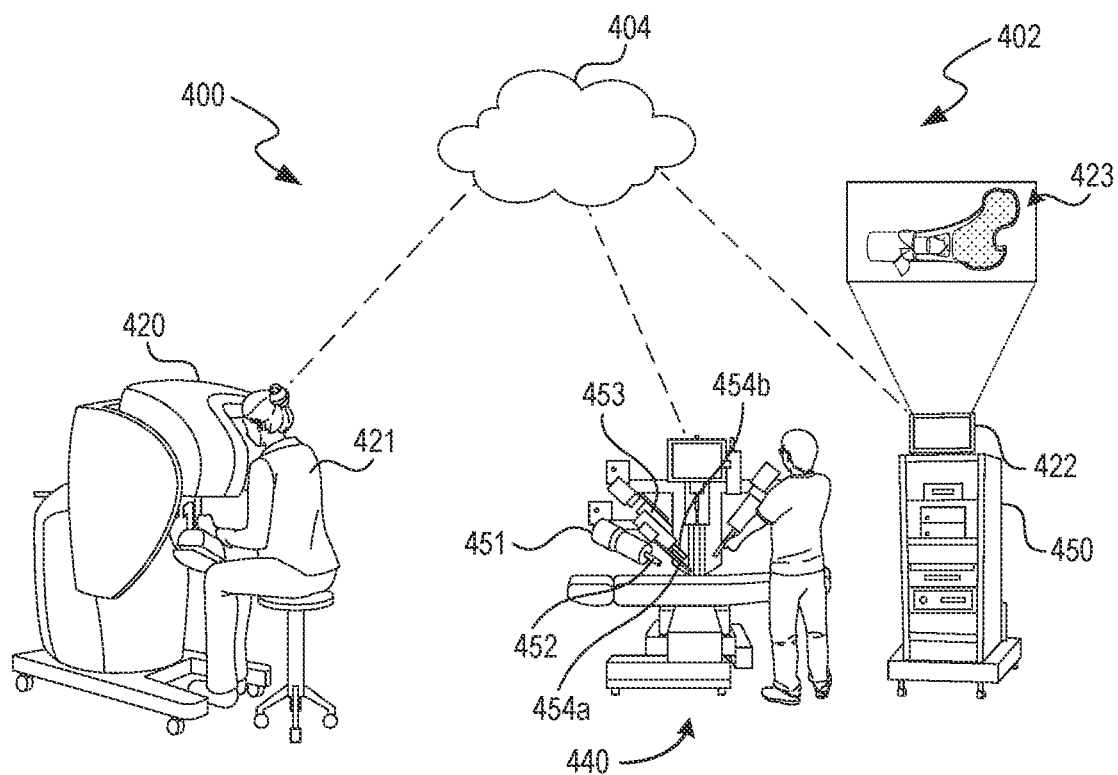
FIG. 4A is a block diagram illustrating an example robotic surgical system, in accordance with one or more embodiments.

FIG. 4A is a block diagram illustrating an example robotic surgical suite or system 400 ("robotic surgical system 400"), in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1). The robotic surgical system 400 can be configured to provide telepresence control by one or more consultants at remote locations based on a pre-operative surgical plan, inter-operative surgical event(s) at the surgical suite, etc. ML algorithms and other techniques disclosed herein can be used to manage surgical suite resources, schedule consultants, manage permission rights, and/or adjust network flow to improve surgical outcomes. For example, flow of network traffic at the surgical suite can be controlled to maintain a threshold level of control of the medical equipment by the user.

The robotic surgical system 400 includes a user device or console 420 ("console 420"), a surgical robot 440, and a computer, controller, or data system 450. The console 420 can be on-site or at a remote location and operated by a surgeon and can communicate with components in a surgical suite or an operating room 402 ("operating room 402"), remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc., or other features disclosed herein to perform surgical step(s) or procedures or implement steps of processes discussed herein.

A consultant device 401 can communicate via the network 404 with components of the robotic surgical system 400, monitoring equipment, or other components of the robotic surgical system 400. The surgical robot 440, or other components disclosed herein, can communicate with and send collected data (e.g., sensor readings, instrument data, surgical robot data, etc.) to at least one database or data system 450, which are accessible to the consultant(s). This information can be used to, for example, create new ML training data sets, generate procedure plans, perform future simulations, post-operatively analyze surgical procedures, or the like. The controller or data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A mobile network test module may measure the latency of the wireless communication established between the robotic surgical system and the consultant device 401 to manage network flow. A measured/determined latency of a wireless network may be the same as a latency of a network that includes the wireless network, where the network may include a starting point/node for data to be transmitted to an ending point/node, and where the data is communicated by one computer/device associated with a surgical site to another computer/device associated with a location of the remote physician/surgeon. Scheduling of consultants can be based, at least in part, on expected latency (e.g., latency within the network 404 or other network) required to perform the telesurgery based on the received one or more surgery data. For example, a scheduling module may be configured to determine the requirement of the bandwidth (e.g., 10 MHz, 20 MHz, 30 MHz, etc.) needed and/or expected latency (e.g., ±50 milliseconds, ±70 milliseconds, ±100 milliseconds, etc.). The parameters for scheduling participation of the consultant device 401 can be selected by a surgical team, healthcare provider, or the like.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to, medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
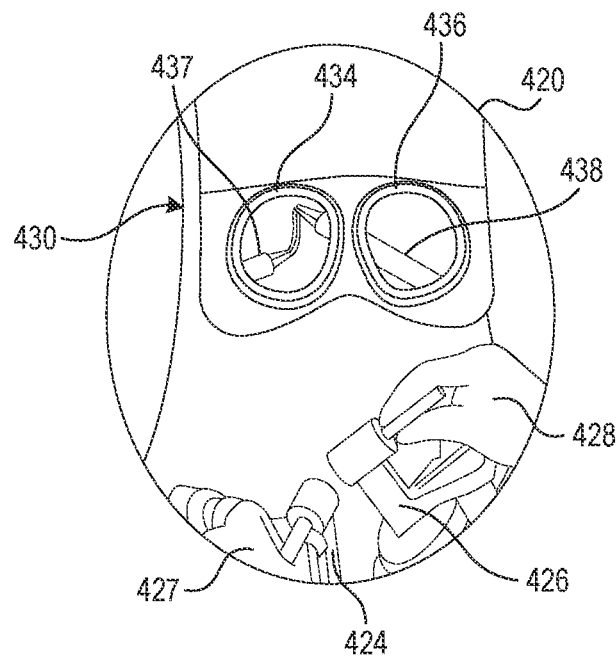
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including multiwavelength images, image modality information, fused data sets, tissue types, mapped images (e.g., tissue types maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452. The surgical robot 440 can include a multi-modality imager 453 having imaging devices 454a, 454b (collectively "imaging devices 454"). The imaging devices 454 can be, for example, PET scanners, ultrasound imagers, MRI imagers, CT scanners, cameras (e.g., camera imager hardware, digital cameras, etc.), infrared imagers, etc. In embodiments, the surgical robot 440 retrieves/receives images from stand-alone X-ray machines, MRI machines, CT scanners, etc. Example imaging devices and imaging modalities are discussed in connection with FIGS. 1, 4A, and 6. The number, imaging capabilities, and configurations of the imaging devices 454 can be selected based on the imaging to be performed.

The robotic surgical system 400 can automatically generate multi-modality images based on surgical plans and then perform one or more surgical steps of a planned surgical procedure. In embodiments, the robotic surgical system 400 analyzes a surgical plan for a patient to generate an imaging plan for obtaining patient information for diagnostic purposes, modifying the surgical plan, performing surgical steps (e.g., one surgical step, multiple surgical steps, all surgical steps), etc. The imaging plan can include, without limitation, one or more regions of interest, targeted information, predicted features of interest, information for diagnostic purposes, or the like. The robotic surgical system 400 can generate the imaging plan based on imaging capabilities of the multi-modality imager 453. The robotic surgical system 400 can notify the surgical team to add or replace imaging devices 454 to achieve the desired imaging capability.

The robotic surgical system 400 can retrieve available images of a patient from, for example, electronic medical records, image databases, and/or other imaging sources. The robotic surgical system 400 can identify and retrieve images that can be processed for producing one or more multi-modality images. The robotic surgical system 400 can determine whether additional unavailable images could be useful for generating multi-modality images that (1) meet at least one threshold criteria (e.g., a confidence score), (2) identify features of interest, (3) have diagnostic capability criteria, etc. In some procedures, the robotic surgical system 400 retrieves available images and determines imaging programs or parameters (e.g., positions, imaging settings, etc.) of one or more of the imaging devices 454 corresponding to the available images. In embodiments, an ML system (see FIG. 2) can be used to generate imaging plans based on training sets. The training sets can include, for example, single modality training sets, composite multi-modality training sets, confirmed diagnostic training sets, and other training sets. This allows the robotic surgical system 400 to perform re-training procedures for continuously or periodically training the ML system. Newly captured images can be keyed to or matched with the retrieved images, thereby increasing accuracy of the multi-modality images. During intro-operative imaging, the images can be analyzed in real-time to further control the robotic surgical system 400.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds. The adverse surgical events can be identified using an ML model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with robotic links, motors, and integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein. As shown by FIG. 4A, the display 422 can display, for example, a diagnosis of tissue, images, maps, surgical plans, etc. For example, the display 422 can display a diagnostic image or map showing, for example, a bone in image 423 (discussed in more detail below with reference to multi-modality imaging), regions of interest (e.g., zones of diseased tissue, regions of tissue with specific characteristic(s), margins, etc.), features of interest, anatomical elements (e.g., cartilage, soft tissue, etc.), or the like. An example image is discussed in connection with FIG. 5. In some embodiments, a diagnostic image can include tissue density, tissue state, identified disease tissue, or the like. The system 402 can use the displayed data to perform one or more surgical steps. A user can view the display 422 to confirm the position of the tissue during the procedure.

Figure 4C:
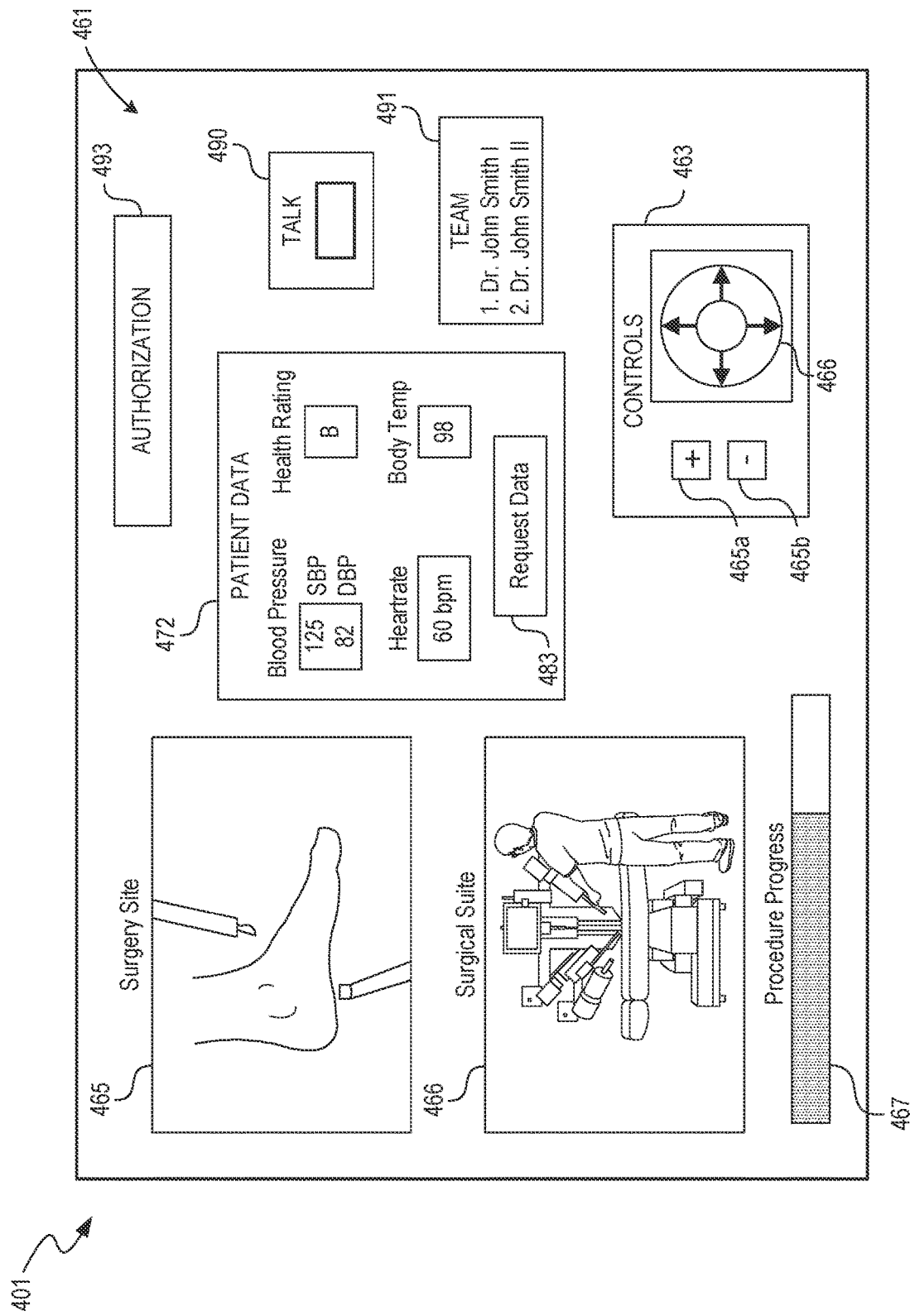
FIG. 4C illustrates an example display of a user device, in accordance with one or more embodiments.

Referring to FIGS. 4A and 4C, the consultant device 401 can display procedure information from the surgery room, equipment controls, and other data disclosed herein. Referring now to FIG. 4C, the consultant device can display a graphical user interface (GUI) 461 for telepresence consulting. The GUI 461 includes an authorization input 493 for authorizing the consultant for participation in a surgical procedure and displays procedure and patient data 465, 466, 472, 491. Imaging equipment can automatically capture images for surgical side viewing via a display 465. The GUI 461 includes a procedure progress 467 that can be updated to show completed progress for the procedure, and controls 463 can be used to operate machines/applications. The user can customize the GUI 461 by rearranging the displayed items for convenience.

The consultant can use an authorization input 493 to, for example, input user authorization information (e.g., access codes, pins, etc.), employee credential information, surgical procedure information (e.g., serial number or code for the surgical procedure), or the like to access and operate equipment. If the consultant needs additional permission rights, the consultant can request the additional permission rights using the authorization input 493. For example, if an adverse event occurs during the procedure requiring the consultant to provide additional care, the consultant can request access to the additional equipment (e.g., robotic arms of surgical robot, breathing machine, heart rate monitor, etc.) via the authorization input 493. The surgical suite system can receive the requested authorization and perform an authorization protocol routine to determine whether the consultant should be granted permission rights to the additionally requested equipment. The surgical suite system can analyze the surgical plan, planned permission rights (e.g., plan of permission rights assigning permission rights to features or steps of the surgical plan), consultant credentials and/or expertise, and/or other information disclosed herein to determine whether to grant permissions. If requested permission rights are denied, the on-site medical team can be notified of the denied request and consultant input, recommendation, etc. If the request is granted, the system can automatically establish communication and control channels for displaying the additional information for the additional equipment via the consultant device 401. The procedure progress 467 can show completed progress for the modified procedure based on the additional equipment.

Dynamic updating of the equipment controls 463 on the consultant device 401 allows the user to acquire control of additional medical equipment in the same consulting session without disrupting communication channels. This reduces the risk of latency and/or network problems that could affect the medical procedure. The controls 463 can be configured to perform all or some of the controls as discussed in connection with FIG. 4B. For example, the controls 463 can include a touch input control module 466 with input features 465a, 465b that can be used to increase or decrease, respectively, settings of equipment. The touch input control module 466 can be used to control movement of, for example, robotic surgical arms, robotic manipulators, and effectors, or the like. For example, the touch input control module 466 can be configured to provide the same controllability as the hand-operated input devices 424, 426 of FIG. 4B. In some embodiments, the controls 463 of FIG. 4C can be modified to include controls for the additional equipment such that the consultant has access to controls for operating newly available equipment in real-time while continuing to view real-time patient data 472. Data collected by and/or associated with additional equipment can automatically be added to the patient data 472.

The consultant device 401 can include a procedure viewer 465, a surgical suite or room viewer 466, and/or other viewers or windows for providing viewing (e.g., real-time or near real-time viewing) of the surgical suite (e.g., viewing at operating rooms, recovery rooms, etc.), medical team, medical equipment, etc. The consultant device 401 can display patient data 472 that can include, for example, blood pressure, health rating, heart rate, body temperature, vitals, physician notes, and/or additional patient data useful to the consultant. To change or receive additional patient data, the consultant can use a request data button 483 to send a message or notification to the on-site surgical team to provide additional patient data. The consultant can use a talk feature 490 to verbally communicate with the surgical team. The consultant device 401 can also display the surgical team information 491. The surgical team information can list physicians, nurses, staff, consultants, and other staffing information.

The robotic surgical system 400, illustrated and described in more detail with reference to FIG. 4A, can further include multiple consultant devices 401 so that multiple members of a surgical team or consultants can view the surgical procedure. The number and configuration of the consultant devices 401 can be selected based on the configuration and number of surgical robots, monitoring equipment, etc. The consultant device 401 can also display procedure data, including a surgical plan (e.g., a surgical plan including completed and future planned surgical steps), patient monitor readings, surgical suite or room information (e.g., available team members, available surgical equipment, surgical robot status, or the like), images (e.g., pre-operative images, images from simulations, real-time images, instructional images, etc.), and other surgical assist information. In some embodiments, the consultant device 401 can be an AR/VR headset, display, or the like.

Referring to FIG. 4A, the robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, California. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through artificial intelligence mapping. The software for artificial intelligence is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system. In some embodiments, the system determines the location, number, angle, and depth of arthroscopic ports (e.g., tubes, rods, etc.) to place in a patient. The system can select the location, number, angle, and depth of the arthroscopic ports based on the maneuverability of the surgical robot, maneuverability of the end effectors of the surgical robot and/or the availability of the surgical tool to place the arthroscopic ports in the patient.

Figure 5:
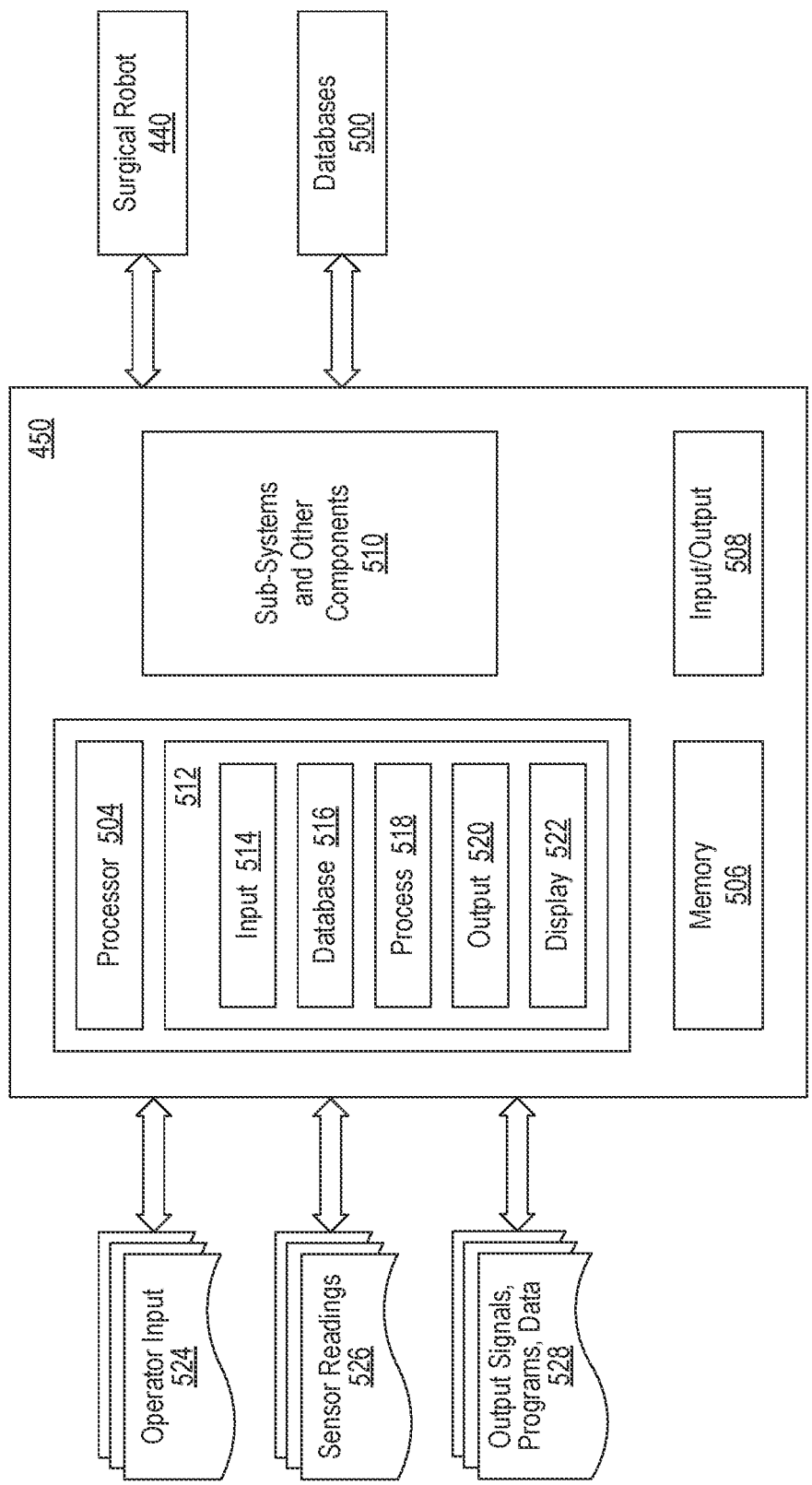
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The controller or data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices (including consultant devices), and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 500. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A network adapter 501 can be an operator authorizing device to manage communications and operation of components, as described with reference to FIG. 3. The network adapter 501 can govern and/or manage permissions to access proxy data in a computer network, track varying levels of trust between different machines and/or applications, and manage control access to surgical equipment, communications between remote devices and the surgical room, etc.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to the patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6A:
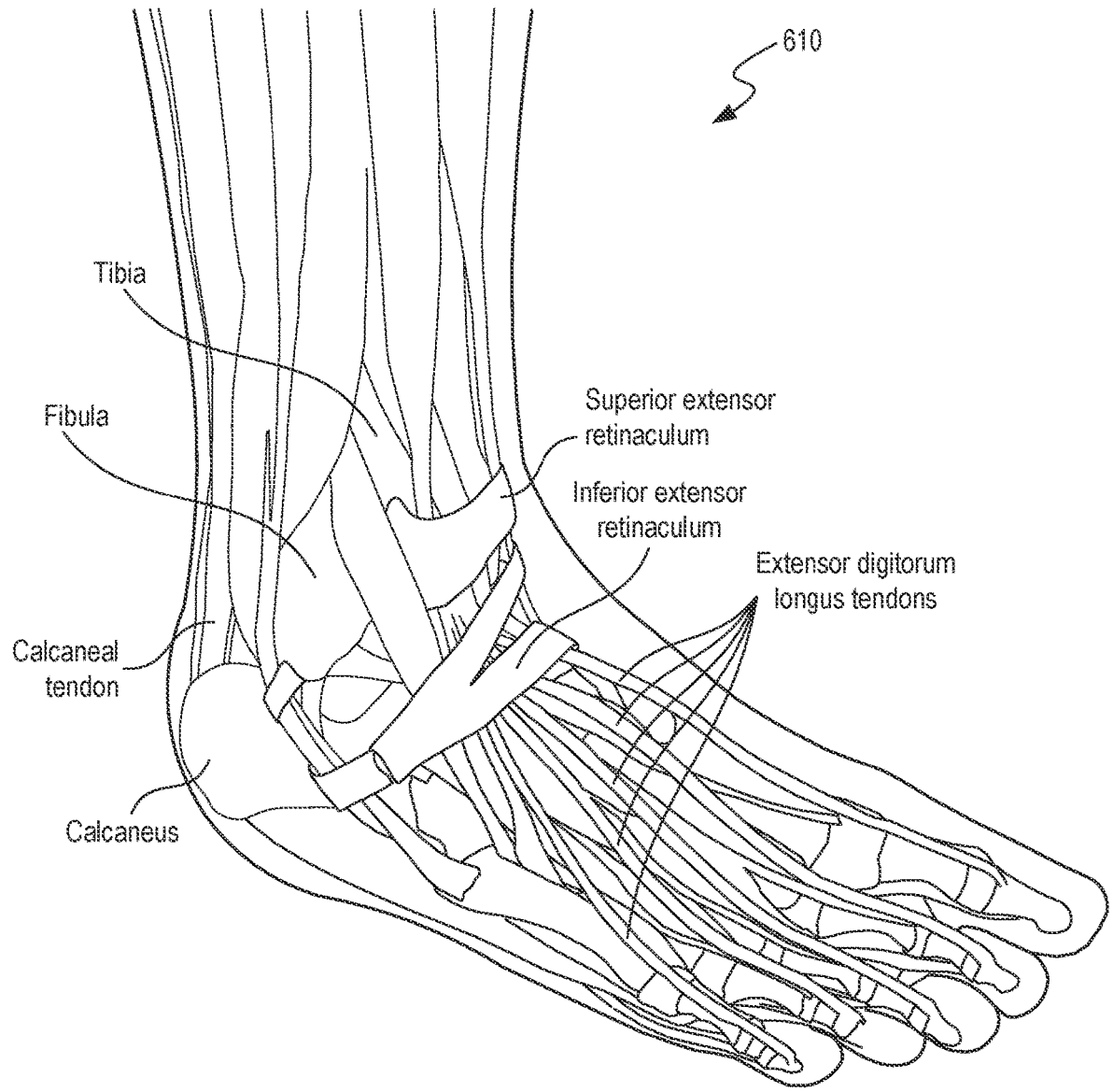
FIG. 6A illustrates an example multi-modality image of a target region, in accordance with one or more embodiments.
Figure 6B:
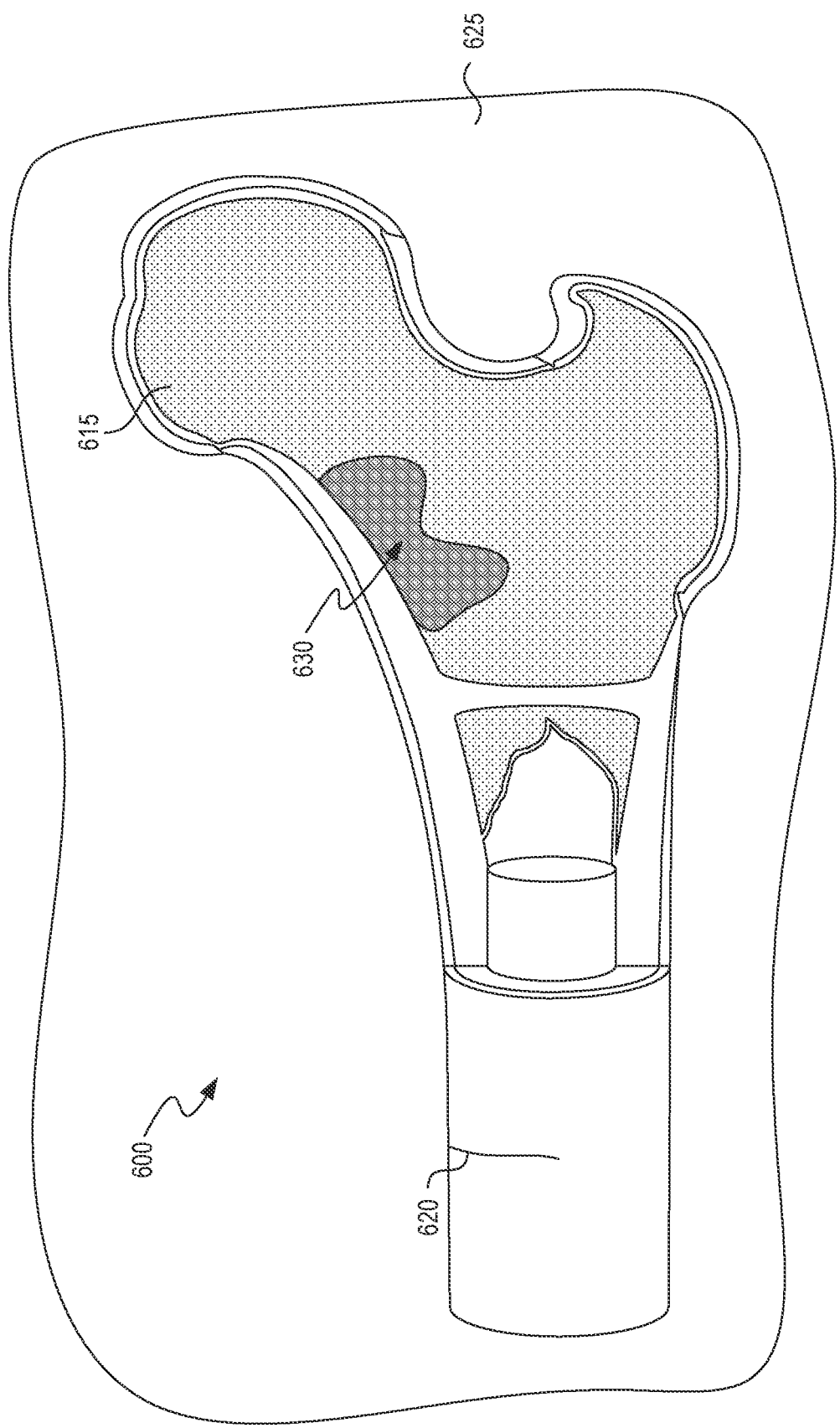
FIG. 6B illustrates an example image of another target region, in accordance with one or more embodiments.

FIG. 6A illustrates an example multi-modality image 600 of a target region, in accordance with one or more embodiments. FIG. 6B illustrates an example of another image 610, in accordance with one or more embodiments. The images 600, 610 can allow a healthcare worker to view a target region 625 to analyze an automated diagnosis, anatomical features, identify tissue of interest, etc. Systems disclosed herein can analyze a surgical plan to identify potential one or more anatomical features of interest. The system can select imaging modalities based on the potential one or more anatomical features of interest and available imaging modalities. The system can obtain at least one image for each imaging modality and generate a multi-modality image based on each of the obtained images. The system can determine one or more imaging characteristics for each potential anatomical feature of interest and correlate imaging characteristics to identify the available imaging modalities used to select the image modalities. The system can identify anatomical features in the image 600 (e.g., a pre-operative image, real-time intraoperative image, etc.). The multi-modality images 600, 610 can be generated based on a surgical plan, physician input, or other input data, and can indicate features (e.g., anatomical elements), margins, tissue type, etc.

Referring to FIG. 6A, to generate the image 600, systems disclosed herein can receive a tissue density image from an MRI device, a bone fracture image from a CT scanner, a bone degeneration or cancerous tissue image from an ultrasound machine, or images from other imagers disclosed herein. In embodiments, the image 600 is generated for a surgical plan for treating a damaged bone and can include, for example, tissue density data 615 (e.g., healthy tissue data from an MRI device), a bone fracture 620 (e.g., identified using a CT scan), diseased tissue 630 (e.g., low-density tissue, cancerous tissue, etc., from ultrasound images), or the like. The system can combine the data to generate the image 600 with features and/or information of interest. In some embodiments, the image 600 highlights regions 625 of a tissue sample according to the diagnoses and/or the values from a multi-modality device or multiple imaging devices.

For example, the image 600 can annotate highlight and/or otherwise identify/emphasize features of interest. The emphasis can help direct the doctor's review of the target region 625 and/or further analysis of the patient. In embodiments, images are generated that include raw data and multi-modality images (e.g., composite images, a multilayer overlaid image, etc.) to allow a physician to perform an independent diagnosis. In embodiments, the raw data is indicated via differences in shading, color, fill patterns, express indications, display tables, selectable displays, and/or in any other suitable manner. Similar processes can be used to generate the image 610.

The multi-modality images 600, 610 of FIGS. 6A and 6B can include selectable layers. For example, the multi-modality images can include a first layer created using a first modality, a second layer created using a second modality, and a third layer created using a third modality. A composite layer can include selected data from one or more of the three layers. The number of layers, number of imaging modalities, types of imaging modalities, data sets, fused data sets, and/or image processing (e.g., scaling of images, filtering of images, etc.) can be selected based on target characteristics of the composite layer, surgical plan (e.g., features of interest, anatomical elements, etc.). For example, the image 600 of FIG. 6 can include selectable layers each with one or more anatomical features identified (e.g., via annotation, false colors, etc.).

FIG. 7 is a block diagram illustrating an example surgical system 700, in accordance with one or more embodiments. The system 700 of FIG. 7 can perform robotic joint arthroscopic procedures based on patient data to improve outcomes. The system 700 can analyze patient joint data to identify and evaluate anatomical structures, tissue (e.g., bone, soft tissue, etc.), biomechanics, and other features of the joints. The surgical system 700 can then perform one or more simulations to develop a robotic-enabled surgical plan that achieves one or more targeted outcomes. Image processing can be applied to patient images (e.g., scans, video, or the like) to determine elasticity, strength, and other properties of soft tissue, such as cartilage, tendons, synovial fluid, or the like. The system 700 can assign properties to structures of the joint to accurately represent the functionality of the joint. This allows simulations to accurately represent complex anatomical structures. Advantageously, the robotic-enabled surgical plan can include surgical steps that can be performed with a higher degree of accuracy than manually performed steps. Additionally, the surgical system 700 can dynamically modify surgical steps based on real-time analysis of the surgical site using machine learning algorithms to improve performance. In some embodiments, the robotic-enabled surgical plan can include both autonomously performed robotic surgical steps and manual surgical steps. This allows a surgical team to participate interactively with the surgical system 700.

Pre-operative simulations can use a virtual patient-specific model that matches the pre-operative anatomy to generate pre-operative surgical plans. Intraoperative data can be used to generate intraoperative virtual models for intraoperative simulations performed to modify pre-operative surgical plans. For example, continuous or periodic intraoperative imaging of a surgical site can be performed to update the virtual model. If a tissue structure is modified (e.g., cut, removed, etc.), the virtual model can be updated accordingly. One or more simulations can then be performed using the modified virtual model to assess predicted outcomes based on the current state of the surgical site. Additionally, the system 700 can determine additional imaging that may be available. For example, when internal tissues are exposed via incisions or ports, the system 700 can automatically image the exposed internal tissue. This allows tissue analyses to be performed using near real-time or real-time acquired data.

The system 700 can be incorporated into or used with technology discussed in connection with FIGS. 1-6B. For example, one or more components of the system of FIG. 7 can be incorporated into the operating room 102 discussed in connection with FIG. 1. By way of another example, user interface 710 and/or imaging device 730 of the system of FIG. 7 can be part of interface 420 discussed in connection with FIG. 4B. Output from the system of FIG. 7 can be transmitted to controller 450 in FIG. 5 and/or various other components disclosed herein. Accordingly, the system of FIG. 7 can be incorporated into robotic surgery systems, or utilized to perform manual surgical procedures or to perform other procedures disclosed herein.

With continued reference to FIG. 7, the system 700 can include a surgical robot 702 configured to perform robotic joint arthroscopic surgery involving the extensor retinaculum. The surgical robot 702 can include the features and components discussed in connection with FIGS. 1-6B. The surgical robot 702 can receive one or more user inputs, workflow objects, and/or data files containing surgical actions for robotic movements. The user inputs can include, without limitation, type of procedure, targeted outcome, physician notes, or other user inputs disclosed herein. The workflow objects can include surgical techniques, surgical steps, surgical processes, etc. The data files can include executable instructions for performing the techniques/processes for specific tools. The surgical robot 702 can determine one or more end effectors and/or surgical tools for performing robotic arthroscopic surgery. The end effectors and/or surgical tools can be displayed by a user interface for selective enabling and/or disabling by the user. The data files can be generated using machine learning algorithms and/or other techniques disclosed herein. In some embodiments, the surgical robot 702 can be designed to assist a surgeon in performing a surgical operation on a patient. The surgical robot 702 can include a controller 704, memory 706, and at least one robotic arm 712 with an end effector 714. Likewise, embodiments of the system of FIG. 7 can include different and/or additional components disclosed herein or can be connected in different ways.

Robotic arthroscopic surgical steps can be displayed on the user interface (e.g., interfaces of displays 401/422, interface or GUI 461, user interface 710) in a sequence to enable execution of the data files containing the robotic movements. The arthroscopic surgical plan can be displayed for pre-operative viewing for surgical planning and/or intraoperative viewing (i.e., while the robotic surgical system robotically operates on the patient) for monitoring the procedure. For intraoperative viewing, the system 700 can determine information to be displayed based on received user input while controlling one or more of the tools operated by the robotic surgical system according to the user input. For example, predicted outcomes can be adjusted based on enabling and/or disabling of a surgical tool. The system 700 can select and display predicted outcomes and can also display surgical steps, surgical plans, patient databases (e.g., patient databases discussed in connection with FIGS. 12 and 14), joint data (e.g., joint data discussed in connection with FIGS. 6B, 12, and 14-16B), or other data. For example, a patient database and associated real-time generated predicted joint movement can be simultaneously displayed while the system 700 controls end effectors or tools.

The system of FIG. 7 automatically designs a surgical workflow for and performs robotic joint arthroscopic surgery. The system of FIG. 7 includes surgical robot 702, which is a robotic system designed to perform or assist a surgeon in performing a surgical operation on a patient. In embodiments, surgical robot 702 includes controller 704, memory 706, and at least one robotic arm 712 having end effector 714. Likewise, embodiments of the system of FIG. 7 can include different and/or additional components or can be connected in different ways.

In embodiments, the system of FIG. 7 performs one or more multi-modality analyses in which one or more multi-sensing devices (e.g., multi-modality imagers, multiple imaging machines, etc.) perform (sequentially or concurrently) multiple scans/tests, such as CT scans, radiation tests, sound tests, optical tests, acoustic tests, photoacoustic tests, combinations thereof, or the like. In embodiments, a multi-modality image can simultaneously image a target region to capture images with matching perspectives relative to the target region such that features from one image can be overlayed onto another, features from multiple images can be stitched together to form a composite image, and/or cross-image features identification can be performed.

The system 700 can perform multi-modality imaging pre-operatively, intraoperatively, and/or post-operatively. Pre-operative images can be used to generate pre-operative plans. Intraoperative images can be used to modify surgical plans, update virtual models of surgical sites, provide monitoring of the surgical procedure to a surgical team, or combinations thereof. Post-operative multiple images can be generated to evaluate the predicted outcome of the procedure, success of the procedure, or the like. In some embodiments, tests are performed during one or more scans of the target region. In a single scan test, the system of FIG. 7 can concurrently perform multiple tests while moving along the tissue sample. In multiple scan tests, the system 700 sequentially performs tests during corresponding scans and/or concurrently performs multiple tests during each scan. The tests can include, without limitation, mobility tests, range of motion tests, stability tests (e.g., lateral angle stability tests), and functional tests (e.g., foot lift tests, functional hop tests, Y-balance tests, etc.), and can be performed for one or more regions of interest. The system 700 can generate scanning/testing protocols for specific joints based on the patient's condition. The system 700 of FIG. 7 can perform different testing, imaging, and/or scanning protocols based on the analysis to be performed. The system 700 can compare pre-operative data and post-operative data to determine prediction accuracy scores for the surgical procedure, rehabilitation protocols, or the like. In response to prediction accuracy scores falling below a threshold score, the machine learning algorithm can be retrained to increase accuracy scores. The system 700 can generate patient-specific rehabilitation protocols based on the post-operative condition of the patient.

The system 700 can generate a virtual model based on captured images and can perform surgical simulations using the virtual model to predict at least one of joint functionality, stability of the joint, or the like. An arthroscopic surgical plan can be modified based on the surgical simulations to achieve at least one of target post-operative functionality, stability of the joint, or other characteristics of the joints. Pre-operative images can be used to perform pre-operative surgical simulations to generate an initial surgical plan.

Intraoperative images can be used to perform intraoperative simulations to allow for adjustments to the surgical plan based on newly captured image data. For example, if an unplanned alteration to tissue occurs, the system 700 can identify the alteration and perform new simulations to determine how the alteration may affect the joint. The system 700 can then generate a modified surgical plan to achieve desired post-operative outcomes.

The system 700 can control imaging equipment to capture images of the altered tissue to generate an alternate or modified surgical plan. In the procedures discussed in connection with FIGS. 12 and 14, the system 700 can acquire and analyze images to determine how to robotically apply one or more sutures to anchors. Post-operative simulations (e.g., functionality simulations, stability simulations, range of motion simulations) can use a real-time three-dimensionally generated virtual model. In some procedures, the system 700 can identify, using image processing techniques, one or more damaged tissue structures contributing to instability of a joint. The system 700 can then determine locations of anchoring and tethers for compensating for the one or more damaged tissue structures so as to, for example, increase stability of the joint while maintaining a predetermined threshold joint functionality value. The predetermined threshold joint functionality value for maintaining a minimum range of motion of the joint can be inputted by the user or determined by system 700. Example ranges of motion of joints are discussed in connection with FIGS. 15, 16A, and 16B.

In embodiments, tests are performed during one or more scans of the target region. In a single scan test, the system of FIG. 7 can concurrently perform multiple tests while moving along the tissue sample. In multiple scan tests, system 600 sequentially performs tests during corresponding scans and/or concurrently performs multiple tests during each scan. The system of FIG. 7 can perform different testing, imaging, and/or scanning protocols based on the analysis to be performed.

The system of FIG. 7 can facilitate communication with another robotic surgical system, doctor, surgeon, or other medical professional by providing results (e.g., multi-modality data, raw data, visualizations of the data, and the like) from the test(s) in real-time. Further, the system of FIG. 7 can combine the results from imaging device(s) to provide a diagnosis of a tissue sample, target region, surgical site, or combinations thereof. In surgical procedures, the results can be automatically transmitted to a surgical robot that analyzes the results to perform one or more surgical steps. Surgical robot 702 can request additional information from the system of FIG. 7 to, for example, complete a surgical step, confirm completion of a surgical step, plan a surgical step, plan a series of surgical steps, or the like. For example, surgical system 402 at FIG. 4A can receive multi-modality results from the system of FIG. 7 to perform a multi-modality-guided robotic surgical step. In embodiments, the results are displayed via display 422 for viewing by the surgical team, as shown in FIG. 4A. Additionally, or alternatively, the results can be viewable via console 420 by user 421 of FIG. 4A while, for example, monitoring or performing one or more surgical steps.

The system of FIG. 7 includes the surgical robot 702 for performing robotic joint arthroscopic surgery to address soft tissue (e.g., ligament, meniscus, labrum, cartilage, joint surface, or the lateral EDL tendon portion of the anatomy). The EDL is situated at the lateral part of the front of the leg. The EDL arises from the lateral condyle of the tibia, from the upper three-quarters of the anterior surface of the body of the fibula, from the upper part of the interosseous membrane, from the deep surface of the fascia, and from the intermuscular septa between the EDL and the tibialis anterior on the medial, and the peroneal muscles on the lateral side. Between the EDL and the tibialis anterior are the upper portions of the anterior tibial vessels and deep peroneal nerve. The EDL passes under the superior and inferior extensor retinaculum of the foot in company with the fibularis tertius, and divides into four slips, which run forward on the dorsum of the foot and are inserted into the second and third phalanges of the four lesser toes. The extensor retinaculum of the arm is located on the back of the forearm, just proximal to the hand. The extensor retinaculum is continuous with the palmar carpal ligament, which is located on the anterior side of the forearm. The superior extensor retinaculum of the leg is the upper part of the extensor retinaculum of the foot, which extends from the ankle to the heelbone.

The surgical robot 702 can request additional information from the system 700 of FIG. 7 to, for example, complete a surgical step, confirm completion of a surgical step, plan a surgical step, plan a series of surgical steps, or the like. For example, the surgical system 402 at FIG. 4A can receive multi-modality results from the system of FIG. 7 to perform a multi-modality-guided robotic surgical step. In embodiments, the results are displayed via display 422 for viewing by the surgical team, as shown in FIG. 4A. Additionally, or alternatively, the results can be viewable via console 420 by a user 421 of FIG. 4A while, for example, monitoring or performing one or more surgical steps.

In embodiments, the surgical robot 702 includes the user interface 710 for accepting control inputs from a user, such as a surgeon or other medical professional. In embodiments, the surgical robot 702 includes a communications interface 708 for transmitting and receiving data to and from a cloud 732 for the purpose of training an artificial intelligence operating within the surgical robot 702 or receiving remote commands from a remote user or an artificial intelligence existing external to the surgical robot 702, e.g., the ML system 200 illustrated and described with reference to FIG. 2. The surgical robot 702 may additionally include a plurality of sensors 716 for providing feedback to the user or an artificial intelligence.

In some embodiments, the user interface 710 can accept control inputs from a user as discussed in connection with FIGS. 4B and 4C. For example, the user interface 710 can include controls discussed in connection with FIG. 4B, the interface 401 discussed in connection with FIG. 4C, or other interfaces disclosed herein. The surgical robot 702 can communicate with one or more devices providing the interface via, for example, a network connection, a direct connection, or other connections disclosed herein.

Controller 704 is a computing device that includes a processor for performing computations and communicates with a memory 706 for storing data. The controller 704 is in communication with a communications interface 708 and may further be allowed to control the at least one robotic arm 712 and end effector 714 of a surgical robot 702. The controller 704 may be a commercially available central processing unit (CPU) or graphical processing unit (GPU) or may be a proprietary, purpose-built design. Multiple controllers 704 may operate in tandem and may be of different types, such as a CPU and a GPU. A GPU is not restricted to only processing graphics or image data and may be used for other computations.

Memory 706 is the electronic circuitry within a computing device that temporarily stores data for usage by the controller 704. The memory 706 may additionally include persistent data storage for storing data used by the controller 704. The memory 706 may be integrated into a controller 704 or may be a discrete component. The memory 706 may be integrated into a circuit, such as soldered on a component of a single board computer (SBC), or may be a removable component such as a discrete dynamic random-access memory (DRAM) stick, secure digital (SD) card, flash drive, solid state drive (SSD), magnetic hard disk drive (HDD), etc. In some embodiments, memory 706 may be part of a controller 704. Multiple types of memory 706 may be used by the surgical robot 702.

Communications interface 708 allows the surgical robot 702 to communicate with external devices and may include a wireless antenna and transceiver or a port for receiving a cable to facilitate a wired connection. Examples of a wired connection include ethernet, USB, or a proprietary connection. A wireless communications interface 708 may include any of Wi-Fi, Bluetooth, NFC, or a cellular communications interface such as 3G, 4G, LTE, or 5G. The communications interface 708 may connect a user interface 710 to the surgical robot 702 or may facilitate access to a local network or a cloud 732 network to access a remote server and/or database.

User interface 710 is a means of interacting with a surgical robot 702 and may include any of a keyboard, computer mouse, trackball, joystick, wireless or wired gamepad, sliders, scroll wheels, touch screen, or microphone for receiving voice commands. The user interface 710 may additionally include any method of interaction of a user with a surgical robot 702 not listed. The user interface 710 may accept direct inputs, such as from a joystick controlling the movement of a robotic arm 712, or indirect inputs, such as commands entered on a keyboard or touch screen to, for example, adjust the sensitivity of a joystick control or the speed of movement of a robotic arm 712 in response to a joystick.

In embodiments, the user interface 710 includes a screen for presenting information to the user such as patient status, imaging data, and navigation data as well as speakers for providing auditory feedback. The user interface 710 may also utilize haptics to provide feedback to the user. In additional embodiments, the user interface 710 includes an AR or VR headset to enable a surgeon to view imagery from at least one imaging device 730 in real-time and may additionally include an overlay, such as highlighting the blood vessels forming a path along which the catheter must be advanced to access the treatment site, such as a blood clot. The user interface 710 may additionally include voice or eye tracking controls.

In embodiments, surgical robot 702 includes a mechanically actuated robotic arm 712 or lever having at least two degrees of freedom. For example, robotic arm 712 is a mechanically actuated arm or lever having at least two degrees of freedom. In embodiments, robotic arm 712 includes one or more end effectors 714 or an imaging sensor. For example, robotic arm 712 typically includes at least one end effector 714 or imaging device 730 and may include both end effector 714 and imaging device 730. Robotic arm 712 may additionally be capable of changing the end effector 714 to facilitate multiple functions and operation of a variety of tools. Robotic arm 712 may be manually controlled or operated in an autonomous or semi-autonomous mode. Surgical robot 702 may have one robotic arm or multiple robotic arms, each of which may be operated independently by one or more users or autonomous systems or a combination of users and autonomous systems.

End effector 714 is the end of a robotic arm 712 that is performing a surgical step. End effector 714 is typically a tool or device for interacting with a physical object and may be a surgical tool intended for acting upon or within a patient or may be a gripping device for securing a separate surgical tool to a robotic arm 712. The end effector 714 may be permanently coupled to the end of a robotic arm 712 or may be detachable, allowing for a system of interchangeable end effectors 714 that may alternatively be selected and swapped by a single robotic arm 712 or multiple robotic arms 712. The end effector 714 may include a catheter or other tool for accessing a treatment site within a patient. Similarly, the end effector 714 may relate to a deployable device, such as a stent, prior to deployment in a patient.

The end effector 714 includes a catheter or other tool for accessing a treatment site within a patient. Similarly, the end effector 714 may relate to a deployable device, such as an anchor, connector, suture, etc. prior to deployment in a patient. The number of tools and configuration of the end effector 714 can be selected based on the procedure to be performed. For example, one or more end effectors 714 can be configured to receive tools in the form of knives, graspers, forceps, suction devices, drills, suturing devices, screws, anchors, lumens, and/or other tools. Simulations with different types of robotic surgery apparatuses, robotic arms, and end effectors can be performed. This allows the system to select surgical suites, surgical robots, robotic arms, end effectors, tools, and other equipment. The system can automatically schedule and order equipment (e.g., surgical kits, tools, or the like) to prepare for the procedure.

In embodiments, end effector 714 includes materials that absorb, reflect, or are transparent to X-rays to facilitate visibility of the end effector 714 when viewed using angiography, fluoroscopy, or other imaging modalities. In embodiments, end effector 714 includes materials that absorb, reflect, or are transparent to X-rays to facilitate the X-rays to pass through to prevent their interference in images. In embodiments, end effector 714 is selectively transparent to X-rays. End effector 714 can be made selectively transparent to X-rays by changing the profile of end effector 714 or by adding X-ray-absorbing or reflective components to end effector 714 to increase or reduce the visibility of end effector 714 to imaging device 730.

Sensor 716 is a measurement tool for monitoring a characteristic or metric associated with surgical robot 702, end effector 714, or a patient. In embodiments, an imaging sensor or imaging device 730 is integrated into a catheter assembly. For example, sensor 716 can be discrete or part of an array or assembly, such as integrated into a catheter. One or more of the sensors 716 can include an electrophysiologic sensor, a temperature sensor, or a thermal gradient sensor. One or more of the sensors 716 can include a barometer, an altimeter, or an accelerometer. One or more of the sensors 716 can include a gyroscope, a humidity sensor, or a magnetometer. One or more of the sensors 716 can include an inclinometer, an oximeter, or a colorimetric monitor. One or more of the sensors 716 can include a sweat analyte sensor, a galvanic skin response sensor, or an interfacial pressure sensor. One or more of the sensors 716 can include a flow sensor, a stretch sensor, a microphone, or a combination thereof.

In embodiments, sensors 716 are integrated into the operation of the surgical robot 702 or may monitor the status of a patient. The data acquired by the sensors 716 may be used to train an ML algorithm used by the surgical robot 702 or artificial intelligence to control the surgical robot 702. In embodiments, imaging device 730 or a sensor 716 includes an X-ray dosimeter configured to monitor an intensity of X-rays emitted toward the patient to prevent a dose of radiation from exceeding a threshold. The threshold can be set at any point between the 300+ millirems of natural sources of radiation and the current federal occupational limit of exposure per year for an adult of 5,000 millirems.

In embodiments, surgical robot 702 is configured to prevent a dose of radiation from exceeding the threshold based on monitoring the intensity of X-rays emitted toward the patient by reducing the intensity of the X-rays. For example, sensors 716 can include an X-ray dosimeter to monitor the intensity of the X-rays being emitted toward the patient to prevent excessive doses of radiation. In embodiments, surgical robot 702 is configured to prevent the dose of radiation from exceeding the threshold based on monitoring the intensity of X-rays emitted toward the patient by reducing a duration in which the X-rays are emitted toward the patient. For example, sensors 716 can be used to reduce the intensity of the X-rays or reduce the duration or increase the interval in which the X-rays are emitted toward the patient to control the dose throughout a procedure.

Base module 718 initiates patient module 720, identification module 722, cut module 724, and suture module 726 using a message, a software or hardware trigger, an interrupt, or another signal. Patient module 720 begins operation by being initiated by the base module 718. Patient module 720 connects to the output module 742. Patient module 720 sends a request to the output module 742 for data stored in the operation database 744. Patient module 720 polls its inputs to receive data stored in the operation database 744 and sent from the output module 742. Patient module 720 receives the data stored in the operation database 744 from the output module 742. Patient module 720 stores the received data in the patient database 728. Patient module 720 returns control to the base module 718.

Identification module 722 begins operation by being initiated by the base module 718. Identification module 722 filters the patient database 728 using terms describing an identification phase of the surgery. In some embodiments, the system of FIG. 7 extracts information describing a surgical procedure to be executed by surgical robot 702 from a surgical database, e.g., patient database 728. In embodiments, the surgical procedure is a robotic arthroscopic surgical procedure, or a robotic surgical procedure for coronary artery bypass. In embodiments, the surgical procedure is a robotic surgical procedure for cutting away cancer tissue from blood vessels, nerves, or important body organs. In embodiments, the surgical procedure is a robotic surgical procedure for gallbladder removal, hip replacement, or hysterectomy. In embodiments, the surgical procedure is a robotic surgical procedure for total or partial kidney removal, kidney transplant, etc.

In embodiments, identification module 722 extracts information describing a surgical procedure stored in patient database 728 for an identification phase. The extracted information is for performing the surgical procedure. For example, the extracted information is a surgical plan (as illustrated and described in more detail with reference to FIGS. 4A-4B and FIG. 5), a series of surgical steps, or a surgical process, or a surgical technique. The information can be expressed as computer instructions, robotic movements, pseudocode, etc. Both the surgical procedure and the information can indicate processes, instructions, or surgical steps to be performed in different phases, at different times, on different regions of the anatomy, or by different robots or end effectors.

In embodiments, sensor data acquired by sensors 716 and imaging device 730 is used to train an ML model for generating the information. An example ML system 200 is illustrated and described in more detail with reference to FIG. 2. Identification module 722 displays information describing a surgical procedure on the user interface 710. Identification module 722 determines whether the user wants to adjust the surgical procedure. If identification module 722 determines that the user has indicated an adjustment to the surgical procedure, identification module 722 prompts the user to enter the adjustment on the user interface 710. Identification module 722 stores information describing the adjustment in the patient database 728.

If identification module 722 determines that the user has not indicated an adjustment, or if an adjustment was already stored in the patient database 728, identification module 722 executes the surgical procedure using surgical robot 702. For example, surgical robot 702 identifies injured soft tissue (e.g., tendon, ligament, meniscus, labrum, cartilage, or joint surface). Soft tissue injury can include laceration, contusion, bruise, sprain, tendonitis, bursitis, stress injuries, or strain. For example, a first end effector secures a first location of a lacerated tendon, and a second end effector secures a second location of the lacerated tendon. Identification module 722 determines whether information describing further surgical steps is stored in the patient database 728. If identification module 722 determines that there is information describing further steps stored in the patient database 728, identification module 722 extracts the information describing the further steps. The system of FIG. 7 displays information describing the extracted information on the user interface 710. If identification module 722 determines that no further steps are indicated by patient database 728, identification module 722 returns control to the base module 718.

Cut module 724 begins operation by being initiated by the base module 718. Cut module 724 filters patient database 728 using terms describing a cutting phase of the surgery. Cut module 724 extracts information describing a surgical procedure stored in patient database 728 for the cutting phase. Cut module 724 displays the information on user interface 710. Cut module 724 determines whether the user has indicated an adjustment to the surgical procedure. If cut module 724 determines that the user has indicated an adjustment, cut module 724 prompts the user to enter the adjustment on the user interface 710. Cut module 724 stores the adjustment in patient database 728.

If cut module 724 determines that the user did not indicate an adjustment, or after cut module 724 stores an adjustment, cut module 724 executes the surgical procedure. Cut module 724 determines whether further surgical steps are indicated by patient database 728. If cut module 724 determines that further surgical steps are indicated, cut module 724 extracts information describing the further steps from patient database 728. The system of FIG. 7 displays information describing the further steps on the user interface 710. If cut module 724 determines that no further surgical steps are indicated, cut module 724 returns control to the base module 718.

Suture module 726 begins operation by being initiated by the base module 718. Suture module 726 filters patient database 728 using terms describing a suture phase of the surgery. Suture module 726 extracts information describing a surgical process, procedure, or technique stored in the patient database 728 for the suture phase. Suture module 726 displays the extracted information on user interface 710. Suture module 726 determines whether the user has indicated an adjustment to the surgical procedure. If suture module 726 determines that the user has indicated an adjustment, suture module 726 prompts the user to enter the adjustment on the user interface 710. Suture module 726 stores the adjustment in the patient database 728. The prompt can be a text prompt, a graphical prompt, an audible prompt (e.g., machine-generated voice prompt), etc. In embodiments, the prompt is an audible prompt emitted by a smart speaker or headphones worn by a surgeon.

If suture module 726 determines that the user did not indicate an adjustment, or if an adjustment was stored in patient database 728, suture module 726 executes the surgical procedure, process, or technique. Suture module 726 determines whether there is a further surgical step stored in the patient database 728. If suture module 726 determines there is a further surgical step stored in the patient database 728, suture module 726 extracts information describing the further step. The system of FIG. 7 displays information describing the further step on the user interface 710. If suture module 726 determines a further surgical step is not indicated by patient database 728, suture module 726 returns control to the base module 718.

Patient database 728 stores information describing a surgical procedure or process that the patient module 720 receives from the output module 742. Patient database 728 can store information describing a patient ID (e.g., JS123), a type of surgery (e.g., EDL tendon repair), or a 3D rendering of the patient's medical images.

Virtual models can be two-dimensional virtual models, three-dimensional models, and other models for representing anatomical features of the patient. The virtual models can have predefining kinematics, properties (e.g., tissue properties, cartilage properties, bone properties, implant properties, suture properties, anchor properties, etc.), dynamic characteristics, or the like. This allows virtual models to accurately represent pre-operative conditions of complex anatomical structures, such as joints. Pre-operative virtual models can represent predicted outcomes for joints, such as improved functionality, stability, or the like. The virtual models can be used to perform simulations to generate simulation data. In some embodiments, virtual models can incorporate or be based on 3D renderings of medical images.

A 3D rendering is a mathematical representation of an object or surface as such object or surface would appear by width, breadth, and depth dimensions. The 3D rendering that is generated transforms the medical images into high-quality, detailed, and lifelike images. The 3D rendering can be generated by the system of FIG. 7. For example, the system of FIG. 7 uses computer graphics processing to generate 3D data and models. The system of FIG. 7 creates a lifelike or non-photorealistic image. The 3D rendering output is a digital file of an object created using software or through 3D scanning.

Patient database 728 can store information describing a phase of the surgery (e.g., identification phase, cutting phase, or suture phase). Patient database 728 can store information describing a surgical process or data files (e.g., a data file for replays of a step as input into CAD GUI 746). Patient database 728 can store information describing (x, y, z) coordinates of the patient's anatomy, surgical tools used, or a technique used (e.g., a threading technique used in the surgery).

Patient database 728 can store information describing calculations (e.g., forces required in certain steps or techniques), materials required for certain steps or techniques, or specialists required for specific steps or techniques. For example, the surgical process for EDL tendon repair surgery can be divided into three phases for the surgical robot 702. The phases are an identification phase, a cutting phase, and a suture phase. In the identification phase, surgical robot 702 uses sensors 716 or imaging device 730 located on end effector 714 to identify the lacerated tendon. In the cutting phase, surgical robot 702 cuts or cleans the lacerated ends of the tendon, to remove fraying. In the suture phase, surgical robot 702 sutures the ends of the lacerated tendon together to repair the tendon.

In some embodiments, the system of FIG. 7 identifies a lacerated tendon of a patient within the patient's anatomy using images of the anatomy. The identification is for performing a robotic arthroscopic surgical procedure for repairing the lacerated tendon. For example, in an identification phase, the system of FIG. 7 identifies the lacerated tendon using digital image analysis and ML, as illustrated and described in more detail with reference to FIG. 2. An ML model can be trained using sensor data and image data from historical and labeled medical images. An ML system extracts features from the images of the anatomy and uses the features to identify the lacerated tendon of the patient.

A first end effector secures a first location of the lacerated tendon, and a second end effector secures a second location of the lacerated tendon. In the cutting phase, a third end effector can secure the first location of the lacerated tendon, and a knife end effector can cut the frayed end of the first location of the lacerated tendon. The knife end effector is removed, and the third end effector releases the first location of the lacerated tendon. Continuing the example, the third end effector secures the second location of the lacerated tendon, and the knife end effector cuts the frayed end of the second location of the lacerated tendon. The knife end effector is removed, and the third end effector releases the second location of the lacerated tendon.

In the suture phase, surgical robot 702 uses a suture end effector to insert an intertendinous suture on a fibula location through a lacerated portion of the tendon. The fibula refers to the calf bone, a leg bone on the lateral location of the tibia, to which it is connected. The fibula is the smaller of the two bones and, in proportion to its length, the most slender of all the long bones. "Intertendinous" refers to sutures between tendon portions. The suture end effector passes the suture proximate to a dorsal surface of the tendon on the fibula location. The term "dorsal" refers to the back or posterior of a structure. For example, dorsal surfaces of a human body are the back, buttocks, calves, and the knuckle side of the hand.

The suture is passed proximate to and ventrally to the tendon. The term "ventral" refers to the front or anterior of a structure. The ventral surfaces of the body include the chest, abdomen, shins, palms, and soles. The suture end effector inserts the suture through a dorsal aspect of the tendon on a tibia location. The tibia refers to the shinbone or shank bone. The tibia is the larger, stronger, and anterior (frontal) of the two bones in the leg below the knee. The suture end effector exits the suture through the lacerated region of the tendon on the tibia location. The process is repeated on the second location of the lacerated tendon and the suture is tied to complete the surgery. These features and anatomy can be labeled in anatomical images, such as the image 610 discussed in connection with FIG. 6B.

The surgical robot 702 can include one or more ML systems trained to correlate feature vectors to expected outputs in the training data. As part of the training of an ML model, the ML system can form a training set of favorable outcomes (e.g., prior patient data with favorable outcomes) and training labels by identifying a positive training set of features that have been determined to have a desired property in question, and, in some embodiments, forms a negative training set of features that lack the property in question. The property in question can include, without limitation, one or more threshold outcomes/scores, therapeutic effect(s), or other criteria selected by, for example, a user or surgical team.

The surgical robot 702 can include a correlation module configured to retrieve data from a surgery database based on the surgery type. The correlation module performs correlations on selected parameter(s) to determine if parameters are highly correlated. The correlation module determines if the correlation coefficient is over the predetermined threshold, for example, over a correlation coefficient (e.g., a predetermined correlation coefficient). If it is determined that the correlation coefficient is over the predetermined threshold, then the correlation module extracts the best match data point from the data set. The correlation module then stores the data entry for the best match data point in a recommendation database. If it is determined that the correlation coefficient is not over the predetermined threshold, or after the data entry for the best match data point is stored in the recommendation database, the correlation module determines if there are more parameters remaining in the surgery database. If it is determined that there are more parameters remaining in the surgery database, the correlation module selects the next parameter in the surgery database and the process returns to performing correlations on the parameters. If it is determined that there are no more parameters remaining in the surgery database, the correlation module returns to the base module.

The recommendation module can begin by being initiated by the base module. The recommendation module filters the recommendation database based on the correlation coefficient (e.g., the highest correlation coefficient). The recommendation module selects the highest correlated data entry in the recommendation database. Other techniques can be used.

For arthroscopic procedures, the training data can include, without limitation, pre-operative data, post-operative data, outcomes (e.g., short-term outcomes, long-term outcomes, etc.), and surgical data (e.g., adverse events, physician input, etc.). For leg-related procedures, the training data can include threshold criteria (e.g., threshold values, threshold scores, etc.), scores (e.g., American Orthopaedic Foot and Ankle Society (AOFAS) score, Visual Analogue Scale (VAS) score, Cumberland Ankle Instability Tool (CAIT) scores, quality of life scores, pain scores, etc.), stress radiographs to measure tilt test (e.g., talar tilt test) and anterior drawer tests, or the like. The threshold criteria can be selected as a favorable outcome. The values/scores can be selected as threshold outcomes or therapeutic effect(s) for approving surgical plans, simulations, etc. For arm-related procedures, the training data can include, without limitation, thresholding values/scores, Disabilities of the Arm, Shoulder, and Hand (DASH) questionnaire scores, etc. The surgical robot 702 can set up and train the ML model as discussed in connection with FIG. 2 and can include one or more ML systems (e.g., ML system 200 of FIG. 2).

The surgical robot 702 can also generate surgical procedures or plans with joint stabilization predictions (e.g., post-operative stability scores of joints, long-term stability scores of joints, etc.), joint mechanics predictions (e.g., one or more target characteristics of joint mechanics), predicted restored function of the joint, combinations thereof, or the like. The surgical robot 702 can manage pain by, for example, determining ligament-attachment joint stabilization steps for utilizing connectors to adjust movement of the joint. For example, the system 700 can identify attachment sites to be physically connected to other structures (e.g., ligaments, bones, muscle, etc.) of the joints. In some implementations, the system 700 can identify one or more attachment points along an anatomical structure (e.g., extensor retinaculum, dorsal carpal ligament, posterior annular ligament, antebrachial fascia, etc.) that are capable of serving as attachment points for limiting motion of the joint, reinforcing the joint, limiting range of motion of the joint, combinations thereof, or the like. Images of the anatomical structure can be analyzed to determine the contribution of the anatomical structure to properties of the joint. The system 700 can then identify the number and position of attachment points based on the desired forces to be applied to the anatomical structures. The properties of implantable connectors can be selected based on target outcomes. For example, unextendible, flexible sutures can connect a ligament to a bone on the opposite side of a joint to limit or fix a range of motion of a joint. This can allow the joint to have normal range of motion in one direction while limiting the range of motion in an opposite direction.

The surgical robot 702 can use one or more ML systems to analyze real-time data (e.g., video, images, etc.) of a surgery site to determine one or more candidate surgical steps, generate predicted outcomes for candidate surgical steps, and/or generate simulations for physician review. As shown in FIG. 4C, a physician can view a surgical site 465 annotated with, for example, labeled structures of a joint, joint mechanics information, plan surgical steps, surgical tools, or the like. The patient data 472 can include, without limitation, target sites (e.g., attachment sites, anchor sites), joint data, mobility data, and other patient data related to the surgical procedure. Example information for display is discussed in connection with FIGS. 6A, 6B, 15, 16A, and 16B. The system 700 can predict post-operative outcomes based on, for example, properties of ligaments, properties of implantable connectors, etc. to improve joint stabilization, limit disease progression, and/or improve patient biomechanics. The predicted post-operative outcomes can be for a selected time or period of time. For example, the system 700 can predict post-operative outcomes one month after surgery, six months after surgery, one year after surgery, two years after surgery, or the like. Age-related changes to anatomical structures, tissue, and other anatomical elements can be used to generate the predicted time-varying post-operative outcomes. By way of example, soft tissue, such as ligaments, may become hardened or lose elasticity over a period of time. The system 700 can predict biomechanics at joints based on such tissue changes. This allows a user to evaluate long-term outcomes of surgical procedures based on typical age-related effects.

The system 700 can generate post-operative outcomes based on different types of simulations. The simulations can include non-linear characteristics (e.g., micromechanics, mechanical behavior, etc.) of soft tissue. Linear, non-linear, and other mechanical properties can be applied to tissue to generate linear finite element models, non-linear finite element models, joint modeling (e.g., linear joint modeling, non-linear joint modeling, dynamic joint modeling, etc.), or the like. For example, the system 700 can model and simulate the dynamic behavior of non-linear anatomical structures of a joint. The dominant characteristics of the joints can be identified and used to determine anatomical features to be modified.

With continued reference to FIG. 7, imaging device 730 is any device capable of collecting data which can be used to create an image, or a representation of a physical structure or phenomena. The terms imaging device and imaging sensor are used interchangeably herein. Imaging device 730 can include any device capable of detecting sound or electromagnetic waves and assembling a visual representation of the detected waves. Imaging devices 730 can collect waves from any part of the electromagnetic spectrum or sounds at any range of frequencies, often as a matrix of independently acquired measurements that each represent a pixel of a 2D or 3D image. These measurements may be taken simultaneously or in series via a scanning process or a combination of methods. Some pixels of an image produced by an imaging device 730 may be interpolated from direct measurements representing adjacent pixels in order to increase the resolution of a generated image.

In embodiments, the system of FIG. 7 obtains images of an anatomy of a patient using an imaging sensor (e.g., imaging device 730) of surgical robot 702 for performing a robotic arthroscopic surgical procedure based on a surgical process. Imaging devices 730 may receive or generate imaging data. Imaging devices 730 can include, for example, cameras attached to the robotic arm 712, cameras mounted to the ceiling or other structure above the surgical theater, or cameras mounted on a tripod or other independent mounting device. Imaging devices 730 can include cameras body worn by the surgeon or other surgical staff, cameras incorporated into a wearable device (e.g., an AR device such as Google Glass or Microsoft HoloLens), or cameras integrated into an endoscopic, microscopic, or laparoscopic device. Imaging devices 730 can include ultrasound devices present in the surgical theater.

Imaging devices 730 can include an algorithm or software module capable of determining qualitative or quantitative data from medical images. The algorithm can be a deep learning algorithm trained on a data set of medical images. Imaging device 730 may further refer to a device used to acquire medical imagery by any means including MRI, CT, or X-ray. Imaging device 730 may further refer to a device used to acquire medical imagery by PET, ultrasound, or arthrography. Imaging device 730 may further refer to a device used to acquire medical imagery by angiography, fluoroscopy, or myelography.

The imaging device 728 can be controlled to acquire images that can be annotated with, for example, patient information, procedure information, or the like. The patient information can include, without limitation, damaged structures of the joint, joint mechanics information (e.g., a range of motion, degrees of freedom, areas contributing to joint instability, motion of FIGS. 15-16B, etc.), ligaments, bone, soft tissue, muscle, synovial sacs, or the like. The procedure information can include, for example, completed surgical steps, planned future surgical steps, information (e.g., calculations, technique information, etc.), attachment sites (e.g., anchor sites, suture sites, etc.), connector information (e.g., number of connectors, dimensions of connectors, properties of connectors, orientation of connectors, routing of connectors, etc.), and other information discussed in connection with FIGS. 1-16B, and other information disclosed herein.

Imaging device 730 can acquire images in real-time or be used to create composite images or models in real-time. Cloud 732 is a distributed network of computers including servers and databases. Cloud 732 may be a private cloud, where access is restricted by isolating the network, such as preventing external access, or by using encryption to limit access to only authorized users. Alternatively, cloud 732 may be a public cloud, where access is widely available via the internet. A public cloud may be unsecured or may include limited security features. Surgical robot network 734 is a network connected to the surgical robot 702 using which surgical robot 702 can receive and send data, provide controls to a user for the surgical robot 702 through a user interface 710, and allow a user to utilize a CAD GUI 746 to design, test, and create a surgical process for a patient.

Surgical robot network (S.R.N.) base module 736 initiates image collection module 738, procedure module 740, and output module 742 using a message, a software or hardware trigger, an interrupt, or another signal. Image collection module 738 begins operation by being initiated by the S.R.N. base module 736. Image collection module 738 connects to the MRI module 750. Image collection module 738 sends a request to the MRI module 750 for data stored in the MRI database 752. Image collection module 738 polls its inputs to receive data stored in the MRI database 752. Image collection module 738 receives the data stored in the MRI database 752 from the MRI module 750. Image collection module 738 stores the received data in the operation database 744.

In embodiments, images of a patient's anatomy include MRI images. An extracted surgical process includes performing a 3D reconstruction from the MRI images for identifying a lacerated tendon. For example, image collection module 738 performs a 3D reconstruction from the MRI images stored in the operation database 744. Image collection module 738 stores the 3D reconstruction to the operation database 744. The image collection module 738 returns control to the S.R.N. base module 736.

A procedure module 740 begins operation by being initiated by the S.R.N. base module 736. The user inputs the patient ID in the CAD GUI 746. The procedure module 740 displays information describing available tools for the surgery on the CAD GUI 746. Then the user selects a tool from the CAD GUI 746. The user performs an action on the CAD GUI 746 using the selected tool. Then the procedure module 740 determines whether the user saved information indicating the tool and the action performed on the CAD GUI 746. If the procedure module 740 determines that information describing the tool and the surgical action performed was not saved, the procedure module 740 prompts the user to select another tool required for the surgery. If the procedure module 740 determines that the user saved information indicating the tool and the action performed, the procedure module 740 determines whether a further step is required in the surgery.

If the procedure module 740 determines that a further surgical step is needed for the surgery, the user is prompted to select a further surgical step in the CAD GUI 746. The procedure module 740 prompts the user to select a surgical tool for the surgery. If the procedure module 740 determines that another step is not required for the surgery, the procedure module 740 stores information describing the tools and actions performed in the operation database 744. The procedure module 740 returns control to the S.R.N. base module 736.

Output module 742 begins operation by being initiated by the S.R.N. base module 736. The output module 742 connects to the patient module 720. The output module 742 polls its inputs to receive a request from the patient module 720 for data stored in the operation database 744. The output module 742 receives a request from the patient module 720 to send the data stored in the operation database 744. The output module 742 sends the data stored in the operation database 744 to the patient module 720. The output module 742 polls its inputs to receive a request from the patient module 720. Output module 742 returns control to the S.R.N. base module 736.

Operation database 744 stores a surgical process that the user inputs in the CAD GUI 746 during the process described with reference to the procedure module 740. Operation database 744 can store information describing a patient ID (e.g., JS123), a type of surgery (e.g., EDL tendon repair), or a 3D rendering of the patient's medical images. Operation database 744 can store information describing a phase of the surgery (e.g., identification phase, cutting phase, or suture phase). Operation database 744 can store information describing a surgical process, data files (e.g., data files for replays of a step as input into the CAD GUI 746), or (x, y, z) coordinates of a patient's anatomy. Operation database 744 can store information describing tools used, techniques used (e.g., a threading technique used in the surgery), or calculations (e.g., forces required in certain steps or techniques). Operation database 744 can store information describing materials required for certain steps or techniques, or specialists required for the specific steps or techniques.

For example, the surgical process for an EDL tendon repair surgery may be broken into three phases for the surgical robot 702, such as the identification phase, the cutting phase, and the suture phase. In the identification phase, surgical robot 702 uses sensors 716 or an imaging device 730 on an end effector 714 to identify the lacerated tendon. In the cutting phase, surgical robot 702 cuts or clean the lacerated ends of the tendon so that they are not frayed. In the suture phase, surgical robot 702 sutures the ends of the lacerated tendon together to repair the tendon. For example, the identification phase includes identifying a lacerated tendon, and securing (by end effectors 714) a first location and a second location of the lacerated tendon. The cutting phase can include securing the first location of the lacerated tendon by a third end effector, and cutting the frayed end of the first location of the lacerated tendon by a knife end effector. The knife end effector is removed, and the third end effector releases the first location of the lacerated tendon. The third end effector secures the second location of the lacerated tendon, and the knife end effector cuts the frayed end of the second location of the lacerated tendon. The knife end effector is removed, and the third end effector releases the second location of the lacerated tendon.

The suture phase can include inserting a suture, by a suture end effector, intertendinously on a fibula location through a lacerated portion of tendon. The suture end effector exits the suture through a dorsal surface of the tendon on the fibula location, and the suture is passed ventrally to the tendon. The suture end effector inserts the suture through a dorsal aspect of the tendon on a tibia location, and the suture end effector exits the suture through a lacerated region of the tendon on the tibia location. The process is repeated on the second location of the lacerated tendon and the suture is tied to complete the surgery.

In embodiments, a surgical process includes at least one surgical step for securing a location of a lacerated tendon. The at least one surgical step is received (e.g., from a surgeon in an operating room or a remote location) using CAD GUI 746. The CAD GUI 746 is a user interface for a computer software system to design surgical processes for patients. CAD refers to the use of computers to aid in the creation, modification, analysis, or optimization of a design, such as a surgical procedure. CAD software is used to increase the productivity of the designer or user, such as a doctor or medical professional, to improve the quality of design, to improve communications through documentation, and to create a database for the procedure. CAD output is often in the form of electronic files for print, machining, or other manufacturing operations.

The GUI, or graphical user interface, is an interface(s) that may either accept inputs from users, provide outputs to users, or perform both actions. In one case, a user can interact with the interface(s) using one or more user-interactive objects and devices. The user-interactive objects and devices may include user input buttons, switches, knobs, levers, keys, trackballs, touchpads, cameras, microphones, motion sensors, heat sensors, inertial sensors, touch sensors, or a combination of the above. Further, the interface(s) may be implemented as a command line interface (CLI), a GUI, a voice interface, or a web-based user interface.

CAD GUI 746 allows a user, such as a surgeon, doctor, medical professional, etc., to view an area of a patient's body that requires surgery in a 3D space. The CAD GUI 746 also allows the user to select various tools, materials, and techniques required for the surgery and allows the user to manipulate the tools, materials, and techniques, as rendered over the patient's 3D image to perform the processes and steps needed for the surgery in a virtual space. The user's movements and actions may be saved and stored in the operation database 744 to assist the surgeon in performing the surgery or to provide the surgical robot 702 with the approximate (x, y, z) coordinates to perform the surgery.

CAD GUI 746 allows other users to view or replay the surgery in the 3D space to alter or adjust movements or actions to perform the surgery. In some embodiments, CAD GUI 746 may provide the user or surgical robot 702 with a list of materials needed, a list of tools required, a workflow process of the surgical procedure, a 3D visual replay of the surgical procedure, etc. A hospital network 748 provides medical information of a patient to the surgical robot network 734, such as electronic health records, medical images (MRIs, X-rays, etc.), a list of the patient's doctors and health care professionals, the patient's current medications and prescriptions, the patient's medical history, the names of the patient's specialists, etc.

MRI module 750 begins operation by connecting to the image collection module 738. MRI module 750 polls its inputs to receive a request from the image collection module 738 for the data stored in the MRI database 752. The MRI module 750 receives a request from the image collection module 738 for the data stored in the MRI database 752. The MRI module 750 sends the data stored in the MRI database 752 to the image collection module 738. The MRI module 750 polls its inputs for a request from the image collection module 738 for the data stored in the MRI database 752. MRI database 752 stores information describing a patient ID (e.g., JS123), a first name of a patient (e.g., John), or a last name of a patient (e.g., Smith).

In embodiments, MRI database 752 stores information describing an anatomical region in which an MRI was taken (e.g., an ankle) or data files (e.g., file JS-Ankle #1.JPEG). In embodiments, MRI database 752 stores information describing MRI data of the patient. MRI is a medical imaging technique that uses a magnetic field and computer-generated radio waves to create detailed images of the organs and tissues in a body. Most MRI machines are large, tube-shaped magnets. When a patient lies inside an MRI machine, the magnetic field temporarily realigns water molecules in the body. Radio waves cause these aligned atoms to produce faint signals, which are used to create cross-sectional MRI images. In some embodiments, the MRI machine can also produce 3D images that can be viewed from different angles.

In some embodiments, the database contains the series of cross-sectional MRI images and stores the data in the sequence they are captured by the imaging device.

The system 700 can analyze the virtually simulated surgical procedures to determine, for example, potential adverse events (e.g., intraoperative adverse events, postoperative adverse events, etc.), risk scores (e.g., risk scores for individual surgical steps or a set of surgical steps), alternative surgical step(s), or the like. In some embodiments, the CAD GUI 746 can generate alternative surgical step(s) and/or surgical procedures to be simulated. Surgical step(s), a sequence of surgical steps, and/or surgical procedures can have associated predicted outcomes, likelihood of outcome scores, and other surgical data. This surgical data can be used to approve, modify, and/or replace the surgical step(s), sequence of steps, and/or procedures.

The CAD GUI 746 can include, without limitation, one or more CAD software modules, simulation modules, finite element analysis (FEA) software modules, and/or software modules disclosed herein. Virtual simulations may be performed such that each virtual implant component is inserted into the anatomy through the virtual access site(s). The virtual implant components may then be virtually installed (e.g., anchored, interconnected, etc.). If the virtual implant component can be navigated from the virtual incision site to the virtual implantation site, the system 700 may approve the surgical plan. In some embodiments, virtual simulations may be performed for connecting or assembling of the virtual components. Implantation sites, anchor sites, number and location of sutures, and other component information may be selected based on virtual simulations and/or predicted patient outcome scores. In some embodiments, the system 700 may rank the scores and may use the ranking to select surgical steps, candidate plans, etc.

In some procedures, the system 700 may select at least one of the anchor site or suture paths along/across joints based on the virtual simulation or the simulation results, including the verified routes or the scores. In some embodiments, a machine learning model (e.g., ML model 216 as illustrated in FIG. 2) may be used to perform the selection of the number and location of anchor sites and/or suture paths. The system and components of FIG. 7 can be implemented using computer hardware, computer software, computer firmware, or a combination thereof. The system 700 can generate a joint restoration plan for assembling a joint assist system. The assembly plan can include, for example, an order for implanting anchors, anchoring or assembly parameters (e.g., minimum forces, minimum torques, maximum forces, maximum torques, tool speeds, etc.), tools, and other data generated based on, for example, access paths, configuration of the joint and surrounding features, the configuration and capabilities of the surgical robot, user input, etc.

In some ankle procedures, one or more sutures can be sewn into the extensor retinaculum at a location determined based on the characteristics of the joint and extensor retinaculum (e.g., thickness, elasticity, etc.) to evaluate ligament re-tensioning (e.g., capsuloligamentous re-tensioning), ligament reinforcement (e.g., extensor retinaculum flap or anchoring), or the like. The system 700 can display a three-dimensional graphic of the ankle being operated on. Surgical tools can be connected to motion sensors and haptic or tactile feedback mechanisms in the simulation. Implantable components can be anchors (e.g., metallic suture anchors, soft suture anchors, biostable suture anchors, screw-in suture anchors, interference fit anchors, etc.), connectors (e.g., sutures, tethers, etc.), and other features. The position, trajectory, orientation, and/or installation parameters for implantable components can be selected based on tissue characteristics (e.g., ligament strength, bone strength, joint motion/loading, etc.), type of installation, or the like.

Figure 8:
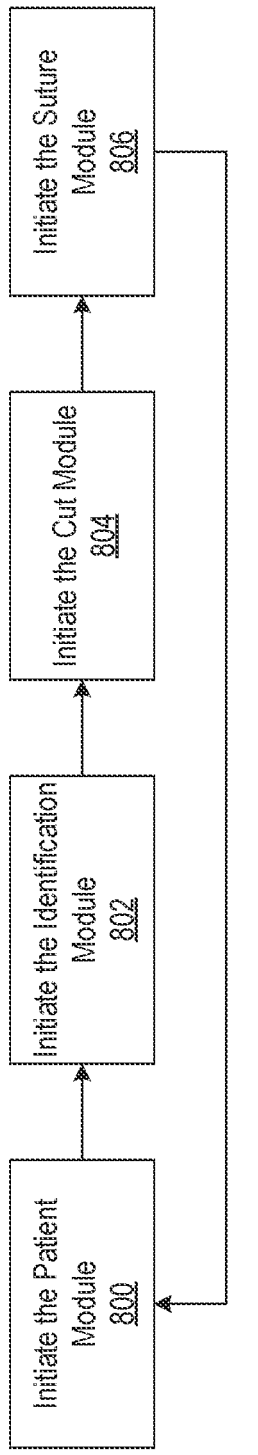
FIG. 8 is a flow diagram illustrating an example process, in accordance with one or more embodiments.

FIG. 8 is a flow diagram illustrating an example process, in accordance with one or more embodiments. An example operating room 102 is illustrated and described in more detail with reference to FIG. 1. In some embodiments, the process of FIG. 8 is performed by the base module 718. The base module 718 is illustrated and described in more detail with reference to FIG. 7. In other embodiments, the process of FIG. 8 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 800, the base module 718 initiates the patient module 720. For example, the patient module 720 begins operation by being initiated by the base module 718 using a message, a software or hardware trigger, an interrupt, or another signal. The patient module 720 connects to the output module 742. Then the patient module 720 sends a request to the output module 742 for the data stored in the operation database 744. The patient module 720 polls its inputs to receive data stored in the operation database 744 from the output module 742. Then the patient module 720 receives the data stored in the operation database 744 from the output module 742. Then the patient module 720 stores the received data in the patient database 728. The patient module 720 returns control to the base module 718. The base module 718 can control operation of imaging device(s) (e.g., imaging devices 454 of FIG. 4A to acquire images.

In step 802, base module 718 initiates identification module 722. For example, identification module 722 begins operation by being initiated by base module 718 using a message, a software or hardware trigger, an interrupt, or another signal. Identification module 722 filters patient database 728 using terms describing an identification phase of the surgery. Identification module 722 extracts information describing a surgical process, procedure, or technique stored in patient database 728 for the identification phase. Identification module 722 displays the extracted information on the user interface 710.

In embodiments, the system of FIG. 7 prompts a user to adjust a robotic arthroscopic surgical procedure being performed. The user is prompted to adjust the procedure using a GUI (e.g., user interface 710) communicatively coupled to surgical robot 702. Responsive to receiving an adjustment to the surgical procedure, the system of FIG. 7 stores information describing one or more surgical steps describing the adjustment in a surgical database (e.g., patient database 728) for adjusting performing of the robotic arthroscopic surgical procedure. For example, identification module 722 determines whether a user has indicated an adjustment to a process or technique. If identification module 722 determines that the user has indicated an adjustment to the process or technique, identification module 722 prompts the user to enter the adjustment on user interface 710. Identification module 722 stores information describing the adjustment in patient database 728. If identification module 722 determines that the user did not indicate an adjustment, or after an adjustment was stored in the patient database 728, identification module 722 executes the process or technique to perform the robotic arthroscopic surgical procedure.

Surgical robot 702 identifies injured soft tissue (e.g., tendon, ligament, meniscus, labrum, cartilage, or joint surface). The soft tissue injury can be laceration, contusion, bruise, sprain, tendonitis, bursitis, stress injuries, or strain. For example, a first end effector secures a first location of the lacerated tendon, and a second end effector secures a second location of the lacerated tendon. Identification module 722 determines whether information describing a further step is stored in patient database 728. If identification module 722 determines that information describing a further step is stored in patient database 728, identification module 722 extracts the information describing the further process or technique stored in patient database 728. The system of FIG. 7 displays the information on user interface 710. If identification module 722 determines that no further step is indicated by the patient database 728, identification module 722 returns control to the base module 718.

In step 804, base module 718 initiates cut module 724. For example, the cut module 724 begins operation by being initiated by the base module 718. The cut module 724 filters the patient database 728 using terms describing a cutting phase of the surgery. Cut module 724 extracts information describing a process or technique stored in the patient database 728 for the cutting phase. The cut module 724 displays information describing the extracted process or technique on the user interface 710. Cut module 724 determines whether a user has indicated an adjustment to the robotic surgical procedure. If cut module 724 determines that a user has indicated an adjustment, the user is prompted to enter the adjustment on the user interface 710. Then the cut module 724 stores information describing the adjustment in the patient database 728.

If cut module 724 determines that the user did not indicate an adjustment, or after an adjustment is stored in the patient database 728, the cut module 724 executes the robotic surgical process. Cut module 724 determines whether a further surgical step is indicated by patient database 728. If cut module 724 determines that a further surgical step is indicated, cut module 724 extracts information describing the step stored in the patient database 728. The system of FIG. 7 displays the information on the user interface 710. If no further surgical step, process, or technique is indicated, cut module 724 returns control to the base module 718.

In step 806, the base module 718 initiates the suture module 726. For example, the suture module 726 begins operation by being initiated by the base module 718. The suture module 726 filters the patient database 728 using terms describing a suture phase of the surgery. For example, the suture module 726 filters the patient database 728 using terms describing the suture process and data files describing surgical robot movements to suture the lacerated ends of the tendon together. Suture module 726 extracts information describing a surgical procedure, process, or technique stored in the patient database 728 for the suture phase. For example, the information includes the steps of (1) inserting an intertendinous suture on a fibula location through a lacerated portion of a tendon, (2) exiting, by a suture end effector, the suture through a dorsal surface of the tendon on the fibula location, (3) passing the suture ventrally with respect to the tendon, (4) inserting the suture through a dorsal aspect of the tendon on a tibia location, (5) exiting the suture through a lacerated region of the tendon on the tibia location, (6) repeating the process on a second location of the lacerated tendon, and (7) tying the suture to complete the surgery.

Suture module 726 displays information describing a surgical procedure, process, or technique on the user interface 710. The terms surgical procedure, surgical process, and surgical technique are used interchangeably herein. In embodiments, the system of FIG. 7 sutures lacerated ends of a tendon by inserting an intertendinous suture on a fibula location of a portion of the lacerated tendon based on the surgical process. The suture is passed through the lacerated tendon on a tibia location. The suture is tied to complete the robotic arthroscopic surgical procedure. For example, a suture end effector inserts an intertendinous suture on the fibula location through a lacerated portion of the tendon. The suture end effector exits the suture through a dorsal surface of the tendon on the fibula location. The suture is passed ventrally to the tendon.

Continuing the example, the suture end effector inserts the suture through a dorsal aspect of the tendon on the tibia side. The suture end effector exits the suture through a lacerated region of the tendon on the tibia side. The process is repeated on the second location of the lacerated tendon and the suture is tied to complete the surgery. Suture module 726 determines whether the user indicated an adjustment to the process or technique. For example, a user (e.g., a surgeon or physician) indicates an adjustment to a surgical process, such as adjusting placement of sutures into the tendon. The user can enter adjusted coordinates for the placement on user interface 710 or change a movement of robotic arm 712 to a desired position. In some embodiments, an adjustment is made using CAD GUI 746. Data describing an adjustment is stored to patient database 728.

If the system of FIG. 7 determines that an adjustment is indicated, the user is prompted to enter the adjustment on the user interface 710. Suture module 726 stores information describing the adjusted procedure in the patient database 728. For example, suture module 726 stores a new location of the sutures with respect to the tendon in the patient database 728. The new location of the sutures can indicate that the sutures should be located a particular distance (e.g., 1 centimeter) higher or lower on the tendon. Updated data (e.g., updated (x, y, z) coordinates or an updated data file for the robotic arm 712) is stored in the patient database 728.

If no adjustment is indicated, or after an adjustment is stored, suture module 726 executes the surgical process. In some embodiments, surgical robot 702 uses a surgical instrument to place a suture below the tendon while inserting another suture on an upper position of the tendon. The instrument is used to perform a two-strand, one-knot sliding-mattress-pattern suture. In some embodiments, surgical robot 702 uses a medical instrument to perform suture techniques, such as a Kessler technique, a modified Kessler technique, or a Pennington variation. In some embodiments, surgical robot 702 uses a medical instrument to perform a Bunnell suture, a Kirchmayr, or an Urbaniak.

In some embodiments, surgical robot 702 uses a medical instrument to perform a Nissim, a Mason, or an Allen. In some embodiments, surgical robot 702 uses a medical instrument to perform a Nicoladoni. Suture module 726 determines whether a further surgical step is indicated by patient database 728. For example, suture module 726 proceeds through information describing surgical steps stored in the patient database 728 until there are no remaining steps. If a further step is indicated, suture module 726 extracts corresponding data from patient database 728. The system of FIG. 7 displays information describing the step on the user interface 710. If no further step is indicated, suture module 726 returns control to the base module 718.

The sutures can be passed through one or more features (e.g., holes, eyelets, etc.) of an anchor. A surgery database can be used to determine an anchor fixation score indicating the force required to remove the implanted anchor. The position and suturing can be displayed for monitoring by a user. Further, suture limbs from the anchors are tied, bringing the ankle mortise into neutral position and stabilizing the ankle joint.

Figure 9:
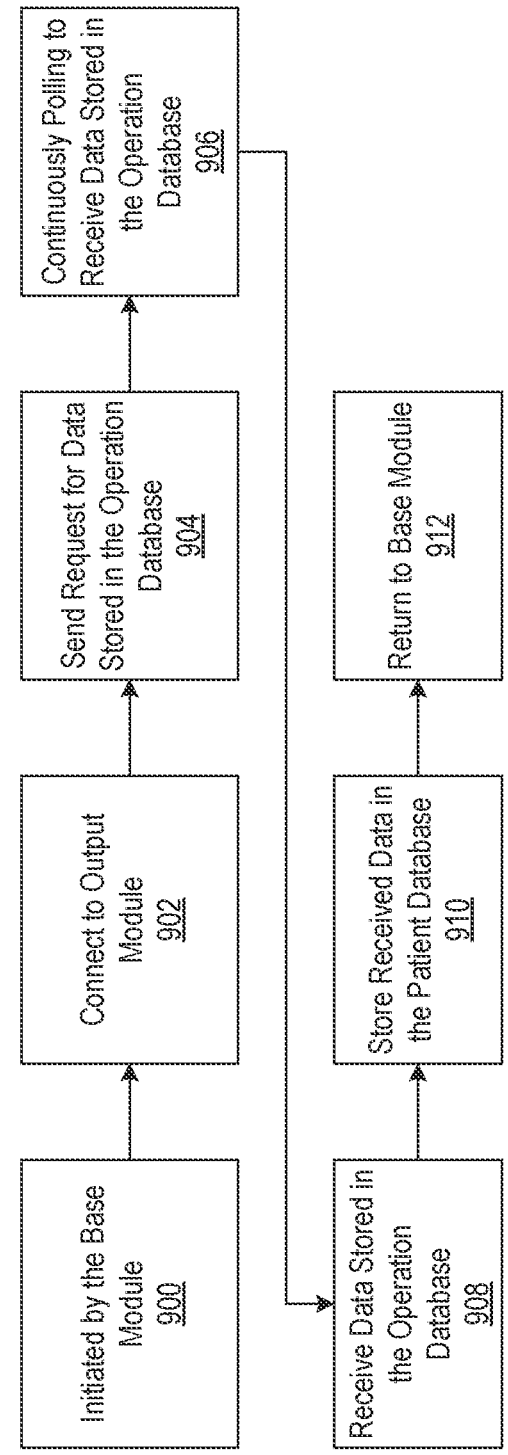
FIG. 9 is a flow diagram illustrating an example process, in accordance with one or more embodiments.

FIG. 9 is a flow diagram illustrating an example process, in accordance with one or more embodiments. An example operating room 102 is illustrated and described in more detail with reference to FIG. 1. In some embodiments, the process of FIG. 9 is performed by the patient module 720. The patient module 720 is illustrated and described in more detail with reference to FIG. 7. In other embodiments, the process of FIG. 9 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 900, the patient module 720 is initiated by the base module 718 using a message, a software or hardware trigger, an interrupt, or another signal. In step 902, the patient module 720 connects to the output module 742. The methods disclosed herein are to treat soft tissue injury (e.g., laceration, contusion, bruise, sprain, tendonitis, bursitis, stress injuries, or strain).

In step 904, the patient module 720 sends a request to the output module 742 to retrieve data stored in the operation database 744. For example, the patient module 720 sends a request to the output module 742 for a patient ID, a type of surgery, or a 3D rendering of a patient's medical images. Output module 742 can retrieve information describing a phase of a surgery, a surgical process, or a data file for replay of a surgical step input into the CAD GUI 746. Output module 742 can retrieve information describing (x, y, z) coordinates of a patient's anatomy, surgical tools used, or techniques used (e.g., a threading technique used in the surgery). Output module 742 can retrieve information describing calculations (e.g., forces required in certain steps or techniques), materials required for certain steps or techniques, or specialists required for the specific steps or techniques.

In step 906, the patient module 720 polls its inputs to receive data stored in the operation database 744 and sent from the output module 742. For example, the patient module 720 polls its inputs to receive data describing a patient ID (e.g., JS123), a type of surgery (e.g., EDL tendon repair), or a 3D rendering of the patient's medical images. The patient module 720 can poll its inputs to receive information describing a phase of the surgery (e.g., an identification phase, a cutting phase, or a suture phase), a surgical process, or data files. The patient module 720 can poll its inputs to receive information describing data files for replays of a surgical step as input into the CAD GUI 746, (x, y, z) coordinates of a patient's body, or tools used. The patient module 720 can poll its inputs to receive information describing surgical techniques used (e.g., a threading technique used in the surgery), calculations (e.g., forces required in certain steps or techniques), or materials required for certain steps or techniques. The patient module 720 can poll its inputs to receive information describing specialists required for specific steps or techniques. The data can include information describing, for example, patient ID, a type of surgery, or a 3D rendering of a patient's medical images (e.g., unannotated, annotated, etc.), image data, near real-time joint simulation data, and/or joint analytic data.

In step 908, the patient module 720 receives the data stored in the operation database 744 from the output module 742. For example, the patient module 720 receives data describing a patient ID, a type of surgery (e.g., EDL tendon repair), or a 3D rendering of a patient's medical images. The patient module 720 can receive data describing a phase of a surgery, a surgical or robotic process, or data files for replays of a step as input into CAD GUI 746. In step 910, the patient module 720 stores the received data in the patient database 728. In step 912, the patient module 720 returns control to the base module 718.

Figure 10:
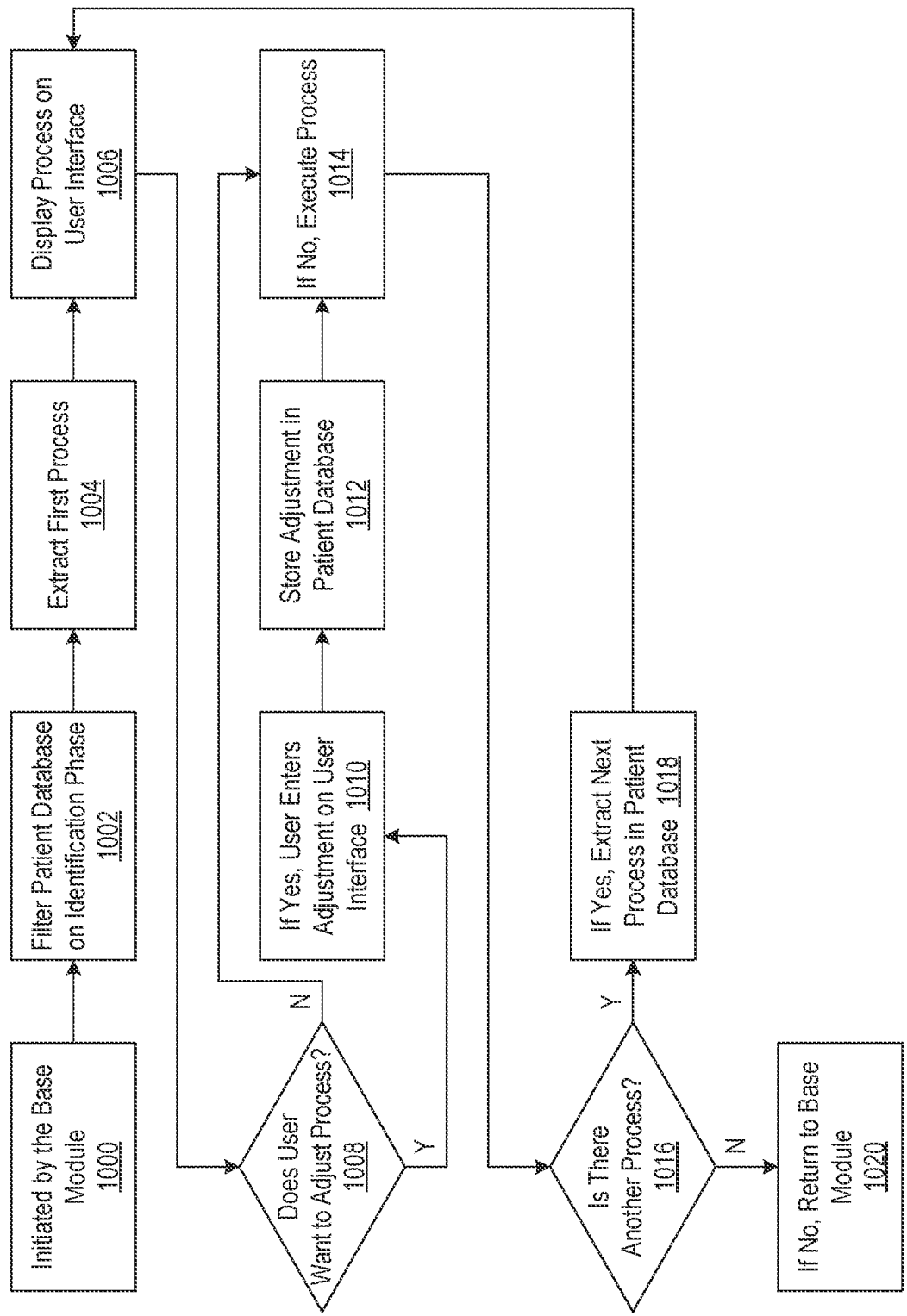
FIG. 10 is a flow diagram illustrating an example process, in accordance with one or more embodiments.

FIG. 10 is a flow diagram illustrating an example process, in accordance with one or more embodiments. An example operating room 102 is illustrated and described in more detail with reference to FIG. 1. In some embodiments, the process of FIG. 10 is performed by the identification module 722. The identification module 722 is illustrated and described in more detail with reference to FIG. 7. In other embodiments, the process is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 1000, the identification module 722 is initiated by the base module 718 using a message, a software or hardware trigger, an interrupt, or another signal. In step 1002, the identification module 722 filters the patient database 728 using terms describing an identification phase of the surgery. For example, the identification module 722 filters the patient database 728 using terms describing a particular surgical process and data files for the movements of the surgical robot 702 to identify and secure injured soft tissue (e.g., tendon, ligament, meniscus, labrum, cartilage, or joint surface). Soft tissue injury can include laceration, contusion, bruise, sprain, tendonitis, bursitis, stress injuries, or strain.

In step 1004, the identification module 722 extracts information describing a surgical process or technique stored in the patient database 728 for the identification phase. For example, the identification module 722 extracts information that identifies a lacerated tendon, a first end effector of the surgical robot 702 for securing a first location of the lacerated tendon, and a second end effector of the surgical robot 702 for securing a second location of the lacerated tendon.

In step 1006, the identification module 722 displays information describing the extracted surgical process on the user interface 710. For example, the identification module 722 displays information describing identifying a lacerated tendon, securing (by a first end effector) a first location of the lacerated tendon, and securing (by a second end effector) a second location of the lacerated tendon.

In embodiments, a surgery is designed to address ankle instability to, for example, improve an outcome score, such as the AOFAS score, VAS score, overall joint score, composite joint score (e.g., composite score based on weighted AOFAS and VAS scores), etc. For example, the ankle can be pre-operatively and/or post-operatively evaluated to generate both pre-operative scores (e.g., AOFAS scores, VAS scores, etc.), and/or post-operative scores. Scores can be used to evaluate the ankles, subtalar, talonavicular, and calcaneocuboid joints, as well as arthrodesis, fractures, arthroplasty, and instabilities. The wrists, hands, shoulders, knee, and other anatomical structures can be scored using different scoring protocols.

A surgery plan can be generated to achieve a threshold score, increase/decrease a pre-operative score(s) (e.g., threshold increase/decrease of AOFAS score, VAS score, respectively), etc. The Brostrom-Gould repair surgery is primarily used to repair the anterior talofibular ligament (ATFL) in the ankle. The recovery time for the procedure varies according to the patient but usually takes a minimum of 3-6 months. The surgery stabilizes the ankle, improves the ankle's mechanics, and restores function. The surgery helps a patient to experience less pain related to his or her injury and ankle sprains, as well as to avoid early arthrosis.

In step 1008, the identification module 722 determines whether the user indicated an adjustment to a surgical process. In some embodiments, a user is prompted to make an adjustment using the CAD GUI 746 so that data describing the adjustment is stored to the patient database 728. In step 1010, if the identification module 722 determines that the user indicated an adjustment, the user is prompted to enter the adjustment on the user interface 710. In step 1012, the identification module 722 stores the adjustment in the patient database 728.

In step 1014, if the identification module 722 determines that the user did not indicate an adjustment, or after an adjustment was stored in the patient database 728, the identification module 722 executes the surgical process. In embodiments, the system of FIG. 7 secures a first location and a second location of a lacerated tendon using (x, y, z) coordinates of a patient's anatomy extracted by surgical robot 702 from a surgical database (e.g., patient database 728). The (x, y, z) coordinates of the anatomy specify the position of any anatomical structure in three-dimensional space using distances to three mutually perpendicular planes (or, equivalently, by a perpendicular projection onto three mutually perpendicular lines). In embodiments, n Cartesian coordinates (an element of real n-space) specify the structure in an n-dimensional Euclidean space for any dimension n. For example, surgical robot 702 identifies the lacerated tendon. A first end effector secures a first location of the lacerated tendon. A second end effector secures a second location of the lacerated tendon.

In embodiments, the surgical robot 702 determines, based on at least one parameter of the surgical robot 702, a number of arthroscopic ports and at least one location for inserting the number of arthroscopic ports into the anatomy. The at least one parameter includes maneuverability of the one or more end effectors or tools of the surgical robot 702. The parameters can include the (x, y, z) coordinates described herein, velocity, acceleration, force, torque of the surgical robot 702, etc.

In step 1016, the identification module 722 determines whether a further step is indicated by patient database 728. For example, the identification module 722 may go through each of the processes and techniques described in the patient database 728 one by one until there are no remaining processes or techniques. In step 1018, if identification module 722 determines that another process or technique is indicated by patient database 728, identification module 722 extracts information describing the process or technique. The system of FIG. 7 displays information describing the process or technique on the user interface 710. In step 1020, if no further surgical process or technique is indicated, identification module 722 returns control to the base module 718.

Figure 11:
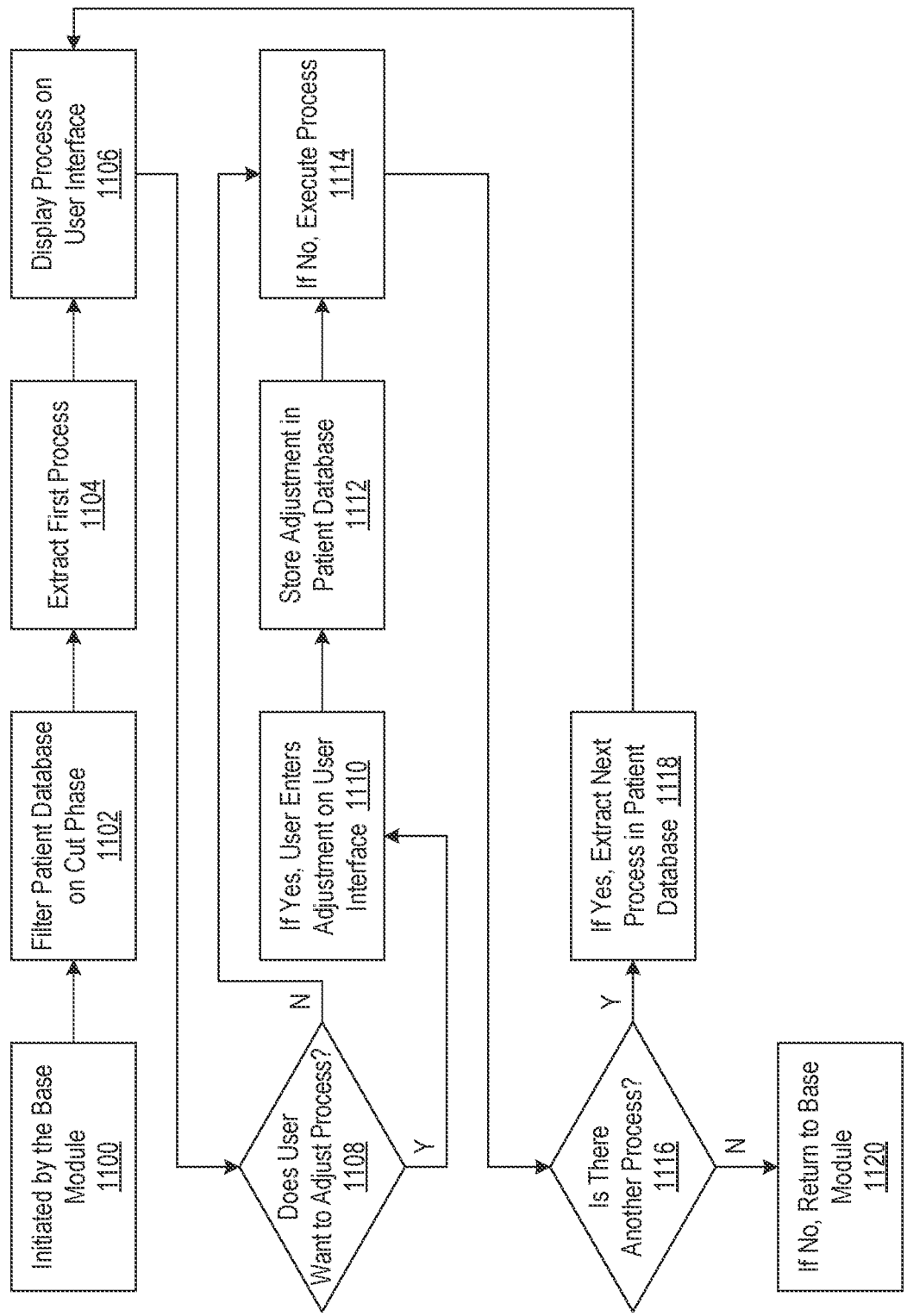
FIG. 11 is a flow diagram illustrating an example process, in accordance with one or more embodiments.

FIG. 11 is a flow diagram illustrating an example process, in accordance with one or more embodiments. An example operating room 102 is illustrated and described in more detail with reference to FIG. 1. In some embodiments, the process of FIG. 11 is performed by the cut module 724. The cut module 724 is illustrated and described in more detail with reference to FIG. 7. In other embodiments, the process of FIG. 11 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 1100, the cut module 724 is initiated by the base module 718 using a message, a software or hardware trigger, an interrupt, or another signal. In step 1102, the cut module 724 filters the patient database 728 using terms describing a cutting phase of the surgery. For example, the cut module 724 filters the patient database 728 using terms describing surgical steps and data files for the movements of the surgical robot 702 to cut or clean up the frayed ends of injured soft tissue (e.g., tendon, ligament, meniscus, labrum, cartilage, or joint surface). Soft tissue injury can be laceration, contusion, bruise, sprain, tendonitis, bursitis, stress injuries, or strain.

In step 1104, the cut module 724 extracts information describing a process or technique stored in the patient database 728 for the cutting phase. For example, cut module 724 extracts information describing (1) securing (by a third end effector) a first location of a lacerated tendon, (2) cutting (by a knife end effector) the frayed end of the first location of the lacerated tendon, (3) removing the knife end effector, (4) releasing the first location of the lacerated tendon, (5) securing a second location of the lacerated tendon, (6) cutting (by a knife end effector) the frayed end of the second location of the lacerated tendon, (7) removing the knife end effector, and (8) releasing the second location of the lacerated tendon.

In step 1106, the cut module 724 displays information describing the extracted process or technique on the user interface 710. In step 1108, the cut module 724 determines whether the user indicated an adjustment to the surgical process. In some embodiments, the user may indicate the adjustment using the CAD GUI 746 so that the data from the adjustment may be stored in the patient database 728.

In step 1110, if the cut module 724 determines that the user indicated an adjustment, the user is prompted to enter the adjustment on the user interface 710. In step 1112, the cut module 724 stores data describing the adjustment in the patient database 728. In step 1114, if the cut module 724 determines that the user did not indicate an adjustment, cut module 724 executes the surgical process. In embodiments, the system of FIG. 7 cuts, by a surgical knife coupled to one or more end effectors 714, the lacerated ends of a tendon to remove frayed material from the lacerated ends. For example, surgical robot 702 can use a third end effector (a knife end effector) to cut the frayed end of the first location of the lacerated tendon. The knife end effector is removed, and the end effectors 714 release the first location of the lacerated tendon. The knife end effector cuts the frayed end of the second location of the lacerated tendon, and the knife end effector is removed. The end effectors 714 release the second location of the lacerated tendon.

In step 1116, the cut module 724 determines whether another process or technique is indicated by patient database 728. In step 1118, if the cut module 724 determines that there is another process or technique stored, cut module 724 extracts information describing the other process or technique. The system of FIG. 7 displays the surgical process or technique on the user interface 710. In step 1120, if the cut module 724 determines that no further surgical process or technique is indicated by patient database 728, cut module 724 returns control to the base module 718.

Figure 12:
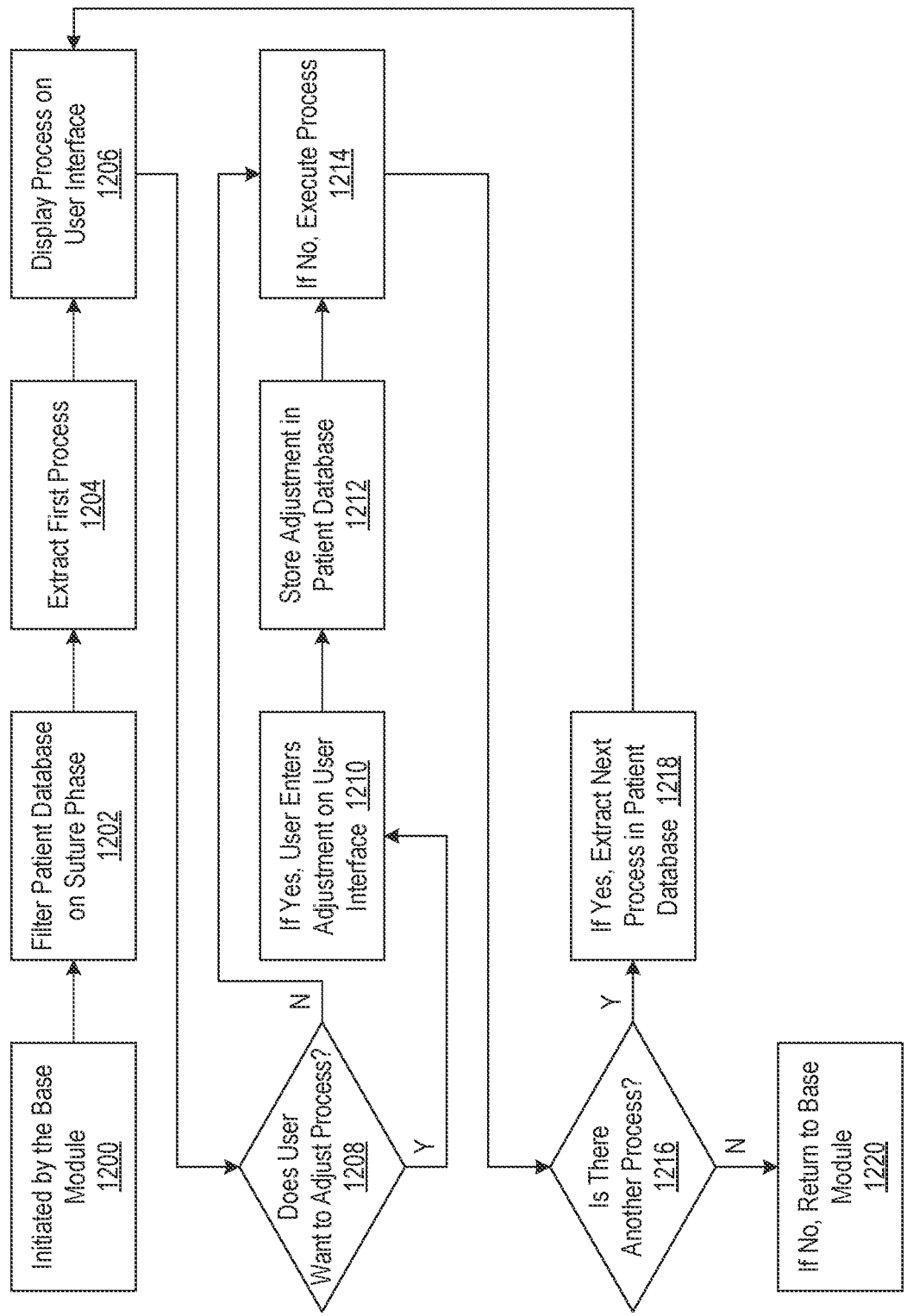
FIG. 12 is a flow diagram illustrating an example process, in accordance with one or more embodiments.

FIG. 12 is a flow diagram illustrating an example process, in accordance with one or more embodiments. An example operating room 102 is illustrated and described in more detail with reference to FIG. 1. In some embodiments, the process of FIG. 12 is performed by the suture module 726. The suture module 726 is illustrated and described in more detail with reference to FIG. 7. In other embodiments, the process of FIG. 12 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 1200, the suture module 726 is initiated by the base module 718 using a message, a software or hardware trigger, an interrupt, or another signal. In step 1202, the suture module 726 filters the patient database 728 using terms describing a suture phase of the surgery. For example, the suture module 726 filters the patient database 728 using terms describing a surgical process and data files for the movements of the surgical robot 702 to suture injured locations of soft tissue (e.g., tendon, ligament, meniscus, labrum, cartilage, or joint surface) together. Soft tissue injury can include laceration, contusion, bruise, sprain, tendonitis, bursitis, stress injuries, or strain.

In step 1204, the suture module 726 extracts information for a surgical process or technique stored in the patient database 728 for the suture phase. For example, the suture module 726 extracts information for inserting an intertendinous suture on a fibula side through a lacerated portion of a tendon, and exiting the suture through a dorsal surface of the tendon on the fibula side. In step 1206, the suture module 726 displays information describing the process or technique on the user interface 710.

In step 1208, the suture module 726 determines whether the user indicated an adjustment to the surgical process. In step 1210, if the suture module 726 determines that the user indicated an adjustment, the user is prompted to enter the adjustment on the user interface 710. In step 1212, the suture module 726 stores data describing the adjustment in the patient database 728.

In step 1214, if the suture module 726 determines that the user did not indicate an adjustment, suture module 726 executes the process or technique. In step 1216, suture module 726 determines whether a further process is indicated by patient database 728. In step 1218, if the suture module 726 determines that a further process is indicated, suture module 726 extracts data describing the further process. The system of FIG. 7 displays the further process on the user interface 710. In step 1220, if suture module 726 determines that no further process is indicated by patient database 728, suture module 726 returns control to the base module 718.

FIG. 13 is a chart illustrating an example database, in accordance with one or more embodiments. The patient database 728 is shown by FIG. 13. In some embodiments, the patient database 728 stores information describing a surgical process that patient module 720 receives from the output module 742. In embodiments, the patient database 728 stores information describing a patient ID (e.g., JS123), a type of surgery (e.g., EDL tendon repair surgery), or a 3D rendering of a patient's medical images. Likewise, embodiments of the patient database 728 can include different and/or additional components or can be arranged in different ways.

In some embodiments, the patient database 728 stores information describing a phase of a surgery, such as an identification phase, a cutting phase, or a suture phase. In some embodiments, the patient database 728 stores information describing a surgical process or data files, including data files for replays of a surgical step input into the CAD GUI 746. In some embodiments, the patient database 728 stores information describing (x, y, z) coordinates of a patient's anatomy, tools used, or techniques used (e.g., a threading technique used in the surgery). Soft tissue injury addressed can be laceration, contusion, bruise, sprain, tendonitis, bursitis, stress injuries, or strain.

In some embodiments, the patient database 728 stores information describing calculations (e.g., forces required in certain steps or techniques), materials required for certain steps or techniques, or specialists required for specific steps or techniques. For example, the surgical process for an EDL tendon repair surgery can be divided into three phases for the surgical robot 702, e.g., an identification phase, a cutting phase, and a suture phase. In the identification phase, the surgical robot 702 uses sensors 716 or an imaging device 730 on the end effector 714 to identify the lacerated tendon. In the cutting phase, the surgical robot 702 cuts or cleans the lacerated ends of the tendon so that they are not frayed. The suture phase allows the surgical robot 702 to suture the ends of the lacerated tendon together to repair the tendon. For example, the identification phase may include identifying the lacerated tendon, a first end effector securing the first location of the lacerated tendon, and a second end effector securing the second location of the lacerated tendon.

In embodiments, the cutting phase includes securing (by a third end effector) a first location of a lacerated tendon, cutting (by a knife end effector) frayed ends of the first location of the lacerated tendon, and removing the knife end effector. In embodiments, the cutting phase includes releasing (by the third end effector) the first location of the lacerated tendon, securing (by the third end effector) a second location of the lacerated tendon, and cutting (by a knife end effector) frayed ends of the second location of the lacerated tendon. In embodiments, the cutting phase includes removing the knife end effector and releasing (by the third end effector) the second location of the lacerated tendon. In the suture phase, a suture end effector inserts a suture on a fibula side through the lacerated portion of the tendon and exits the suture through a dorsal surface of the tendon on the fibula side. The suture is passed ventrally to the tendon, and the suture end effector inserts the suture through a dorsal aspect of the tendon on a tibia side. The suture end effector exits the suture through the lacerated region of the tendon on the tibia side. The process is then repeated on the second location of the lacerated tendon, and the suture is tied to complete the surgery.

Figure 14:
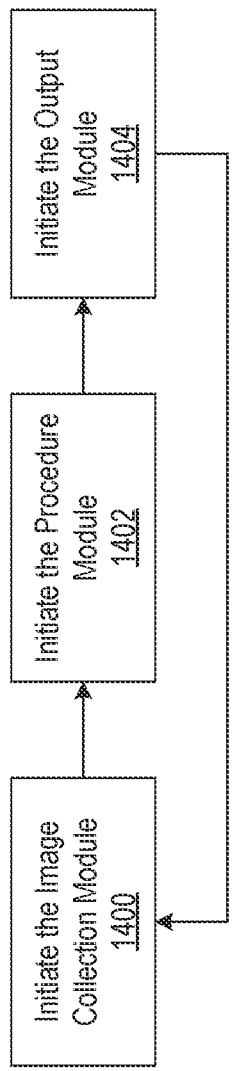
FIG. 14 is a flow diagram illustrating an example process, in accordance with one or more embodiments.

FIG. 14 is a flow diagram illustrating an example process, in accordance with one or more embodiments. An example operating room 102 is illustrated and described in more detail with reference to FIG. 1. In some embodiments, the process of FIG. 14 is performed by the S.R.N. base module 736. The S.R.N. base module 736 is illustrated and described in more detail with reference to FIG. 7. In other embodiments, the process of FIG. 14 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 1400, the S.R.N. base module 736 initiates the image collection module 738. For example, the image collection module 738 begins operation by being initiated by the S.R.N. base module 736 using a message, a software or hardware trigger, an interrupt, or another signal. The image collection module 738 connects to the MRI module 750. The image collection module 738 sends a request to the MRI module 750 for the data stored in the MRI database 752. The image collection module 738 polls its inputs to receive data stored in the MRI database 752. The image collection module 738 receives the data stored in the MRI database 752 from the MRI module 750. Then the image collection module 738 stores the received data in the operation database 744. Then the image collection module 738 performs a 3D reconstruction from the MRI images stored in the operation database 744. Image collection module 738 stores the 3D reconstruction to the operation database 744. Image collection module 738 returns control to the S.R.N. base module 736.

In step 1402, the S.R.N. base module 736 initiates the procedure module 740. For example, the procedure module 740 begins operation by being initiated by the S.R.N. base module 736 using a message, a software or hardware trigger, an interrupt, or another signal. The user inputs the patient ID in the CAD GUI 746. Then the procedure module 740 displays information describing available tools for the surgery on the CAD GUI 746. Then the user selects a tool from the CAD GUI 746. The user performs an action on the CAD GUI 746 using the selected tool.

Procedure module 740 determines whether information describing the tool and the action performed on the CAD GUI 746 was saved. If procedure module 740 determines that information describing the surgical tool and the surgical step performed was not saved, S.R.N. base module 736 prompts the user to select a tool required for the surgery. If procedure module 740 determines that information describing the surgical tool and the surgical step performed was saved, procedure module 740 determines whether a further surgical step is required in the surgery. If procedure module 740 determines that a further surgical step is required for the surgery, the user is prompted to add a surgical step using the CAD GUI 746. The procedure module 740 prompts the user to select a tool for the surgery. If procedure module 740 determines that a further surgical step is not required, procedure module 740 stores information describing the tools and actions performed in the operation database 744. Procedure module 740 returns control to the S.R.N. base module 736.

In step 1404, the S.R.N. base module 736 initiates the output module 742. For example, the output module 742 begins operation by being initiated by the S.R.N. base module 736 using a message, a software or hardware trigger, an interrupt, or another signal. The output module 742 connects to the patient module 720. The output module 742 polls its inputs to receive a request from the patient module 720 for data stored in the operation database 744. The output module 742 receives a request from the patient module 720 to send the data stored in the operation database 744. The output module 742 sends the data stored in the operation database 744 to the patient module 720. The output module 742 polls its inputs to receive a request from the patient module 720. Output module 742 returns control to the S.R.N. base module 736.

Figure 15:
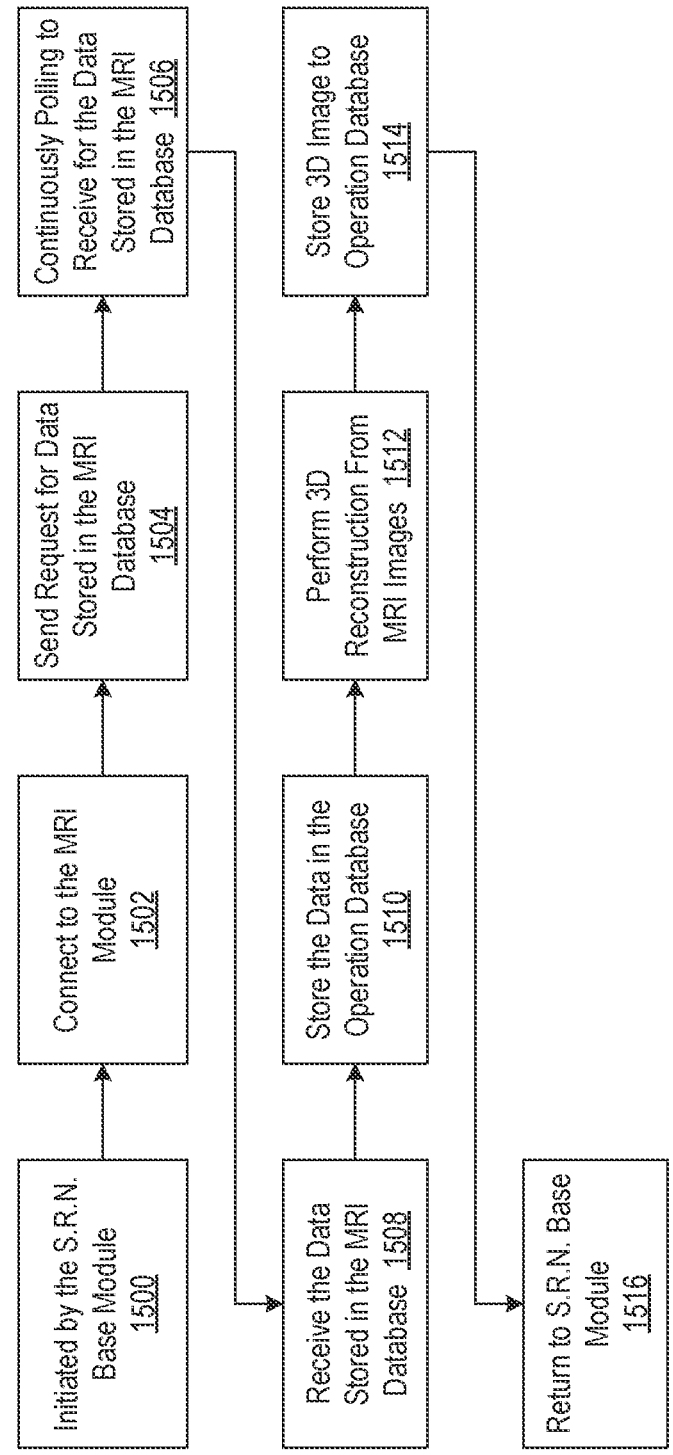
FIG. 15 is a flow diagram illustrating an example process, in accordance with one or more embodiments.

FIG. 15 is a flow diagram illustrating an example process, in accordance with one or more embodiments. An example operating room 102 is illustrated and described in more detail with reference to FIG. 1. In some embodiments, the process of FIG. 15 is performed by the image collection module 738. The image collection module 738 is illustrated and described in more detail with reference to FIG. 7. In other embodiments, the process of FIG. 15 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 1500, the image collection module 738 is initiated by the S.R.N. base module 736 using a message, a software or hardware trigger, an interrupt, or another signal. In step 1502, the image collection module 738 connects to the MRI module 750. In step 1504, the image collection module 738 sends a request to the MRI module 750 to retrieve data stored in the MRI database 752. For example, the image collection module 738 sends a request for the data stored in the MRI database 752 such as a patient ID, a first name of the patient, a last name of the patient, an anatomical region in which the MRI was taken, or data files (e.g., file JS-Ankle #1.JPEG). The database 752 contains MRI data of the patient.

In step 1506, the image collection module 738 polls its inputs to receive data stored in the MRI database 752. For example, the image collection module 738 polls its inputs to receive information describing a patient ID (e.g., JS123), a first name of a patient (e.g., John), or a last name of a patient (e.g., Smith). In embodiments, the image collection module 738 polls its inputs to receive information describing an anatomical region for which the MRI was taken, such as the ankle, and the data files, such as JS-Ankle #1.JPEG.

In step 1508, the image collection module 738 receives the data stored in the MRI database 752 from the MRI module 750. In step 1510, the image collection module 738 stores the received data in the operation database 744.

In step 1512, the image collection module 738 performs a 3D reconstruction from the MRI images stored in the operation database 744. For example, the image collection module 738 may use the received series of MRI images and stitch or combine them together to form a 3D representation of the patient's medical images to be used and viewed in a 3D space in the CAD GUI 746.

In embodiments, the system of FIG. 7 generates a 3D rendering of patient images based on the extracted surgical process. Identifying a lacerated tendon is performed using the 3D rendering. For example, in step 1514, image collection module 738 stores the 3D rendering to operation database 744. Image collection module 738 can store the 3D rendering of the patient's medical images in the operation database 744 to be used by the CAD GUI 746. In step 1516, image collection module 738 returns control to the S.R.N. base module 736.

Figure 16:
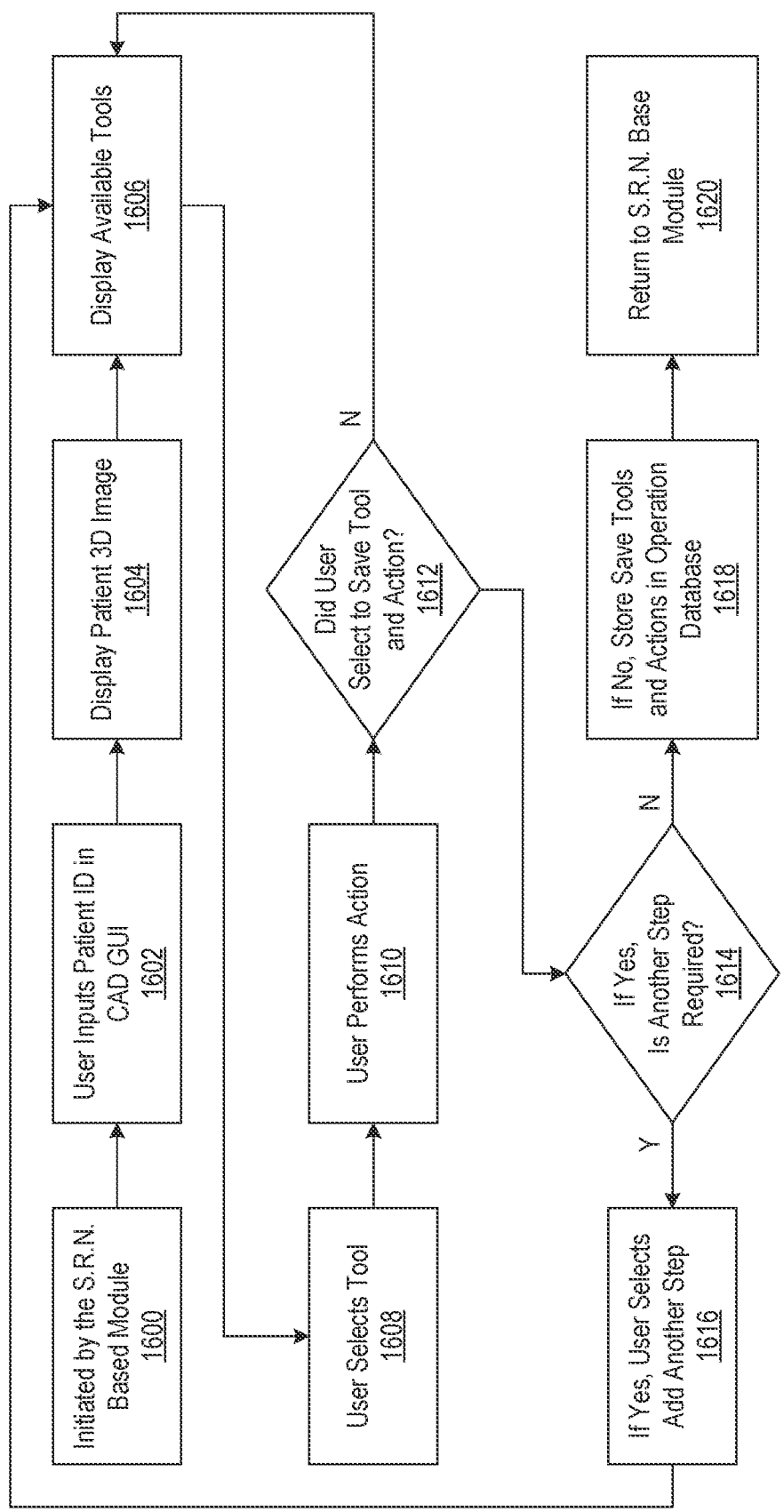
FIG. 16 is a flow diagram illustrating an example process, in accordance with one or more embodiments.

FIG. 16 is a flow diagram illustrating an example process, in accordance with one or more embodiments. An example operating room 102 is illustrated and described in more detail with reference to FIG. 1. In some embodiments, the process of FIG. 16 is performed by the procedure module 740. The procedure module 740 is illustrated and described in more detail with reference to FIG. 7. In other embodiments, the process of FIG. 16 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 1600, the procedure module 740 is initiated by the S.R.N. base module 736 using a message, a software or hardware trigger, an interrupt, or another signal. In step 1602, the system of FIG. 7 determines that the CAD GUI 746 has received a patient ID input by the user. For example, a physician or surgeon inputs a patient ID (such as JS123) to display information related to a patient on the CAD GUI 746. The information can describe a 3D medical image of an anatomical area for a surgical procedure, the specific procedure required, or tools selected for the procedure. In some embodiments, the CAD GUI 746 displays information describing a medical condition of a patient, medications or prescriptions for the patient, or physicians or medical professionals who have worked with the patient.

In step 1604, the procedure module 740 displays a 3D image of a patient on the CAD GUI 746. For example, the procedure module 740 displays a 3D rendering of a patient's medical images in a virtual space, allowing the 3D rendering to be manipulated, altered, or changed, to enable a surgeon to perform a virtual surgical procedure. The virtual surgical procedure generates and stores information describing surgical tools used or surgical actions performed. The system of FIG. 7 can replay the surgical actions performed for future use on a patient. The virtual surgical procedure generates and stores information describing (x, y, z) coordinates of a region of the patient. The virtual surgical procedure generates and stores information describing surgical tools used and surgical actions performed with respect to the (x, y, z) coordinates. The stored information is used by the surgical robot 702 to perform the procedure on a patient.

In step 1606, the procedure module 740 displays information describing available surgical tools on the CAD GUI 746. For example, the procedure module 740 displays information describing tools available for the surgery or surgical procedure, such as knife, straight grasper, basket forceps, suction devices, a plurality of drills, sutures, screws, lumens, etc.

In step 1608, the procedure module 740 determines that the user has indicated a tool selection on the CAD GUI 746. For example, the user has selected any of the multiple tools available (e.g., a knife, a straight grasper, basket forceps, suction devices, multiple drills, sutures, screws, anchors, or lumens). The procedure module 740 determines that the user has indicated an action on the 3D rendering with the selected tool.

In step 1610, the user performs an action on the CAD GUI 746 using the selected tool. For example, the user may input the process for EDL tendon repair surgery in the CAD GUI 746. The surgical process may be broken into different phases for the surgical robot 702, such as the identification phase, the cutting phase, and the suture phase. The identification phase allows the surgical robot 702 to use sensors 716 or an imaging device 730 on an end effector 714 to identify the lacerated tendon. The cutting phase allows the surgical robot 702 to cut or clean the lacerated ends of the tendon so that they are not frayed. The suture phase allows the surgical robot 702 to suture the ends of the lacerated tendon together to repair the tendon.

In step 1612, the procedure module 740 determines whether the user saved the information describing the tool and the action performed on the CAD GUI 746. If procedure module 740 determines that information describing the tool and the action performed on the CAD GUI 746 was not saved, procedure module 740 prompts the user to select a tool for the surgery.

In step 1614, if the procedure module 740 determines that data describing the tool and the action performed was saved, the procedure module 740 determines whether another step is required in the surgery. For example, if data describing a tool and the action performed was saved, the data is stored in the operation database 744 including the (x, y, z) data in relation to the patient's 3D image. In some embodiments, the saved action allows the manipulated or altered 3D image to be stored for the next step in the surgical process. For example, if an incision knife was selected, and an incision was made on a specific region of the ankle, data describing a replay of the knife cutting the skin is stored as well as the (x, y, z) coordinates of the incision knife throughout the process and the coordinates of where the incision occurred on the 3D image. The next step in the surgical process, once saved, displays information describing the ankle with the incision that was previously performed.

In step 1616, if the procedure module 740 determines that another step is required for the surgery, procedure module 740 prompts the user to add another step in the CAD GUI 746. Procedure module 740 prompts the user to select a tool required for the surgery. In step 1618, if the procedure module 740 determines that another step is not required for the surgery, the procedure module 740 stores data describing the tools and actions performed in the operation database 744. In step 1620, the procedure module 740 returns control to the S.R.N. base module 736.

Figure 17:
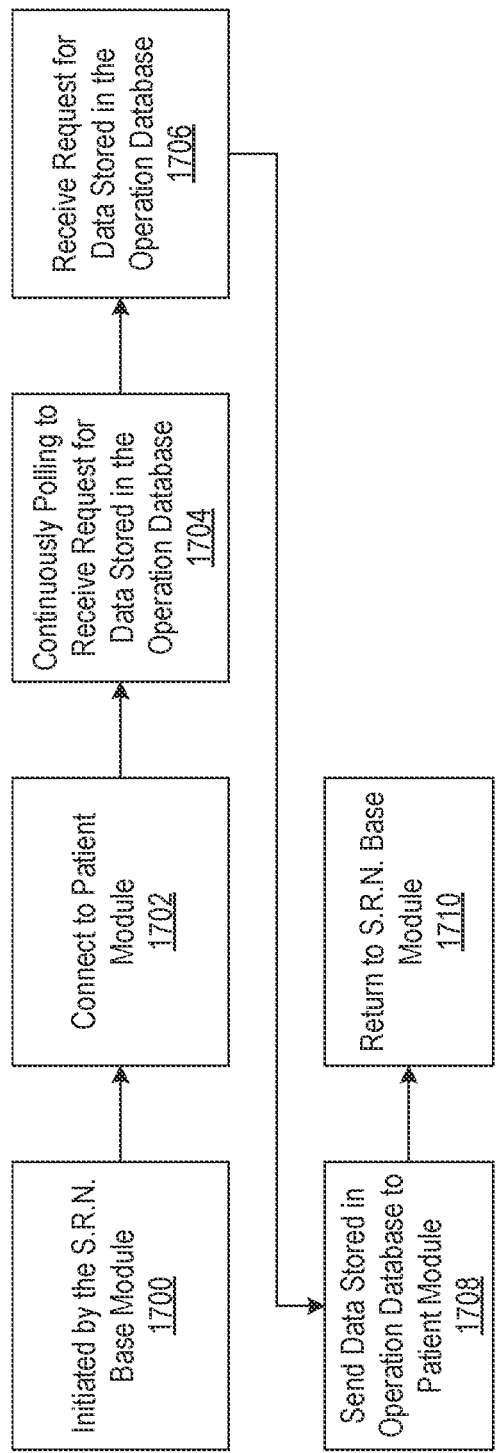
FIG. 17 is a flow diagram illustrating an example process, in accordance with one or more embodiments.

FIG. 17 is a flow diagram illustrating an example process, in accordance with one or more embodiments. An example operating room 102 is illustrated and described in more detail with reference to FIG. 1. In some embodiments, the process of FIG. 17 is performed by the output module 742. The output module 742 is illustrated and described in more detail with reference to FIG. 7. In other embodiments, the process of FIG. 17 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 1700, the output module 742 is initiated by the S.R.N. base module 736 using a message, a software or hardware trigger, an interrupt, or another signal. In step 1702, the output module 742 connects to the patient module 720. In step 1704, the output module 742 polls its inputs to receive a request from the patient module 720 for data stored in the operation database 744. For example, the output module 742 polls its inputs to receive information describing a patient ID (e.g., JS123), a type of surgery (e.g., EDL tendon repair), or a 3D rendering of a patient's medical images.

In embodiments, the output module 742 polls its inputs to receive information describing a phase of a surgery (e.g., an identification phase, a cutting phase, or a suture phase). In embodiments, the output module 742 polls its inputs to receive data describing a surgical process, data files for replays of a surgical step as input into the CAD GUI 746, or (x, y, z) coordinates of a patient's anatomy. In embodiments, the output module 742 polls its inputs to receive data describing tools used, surgical techniques used (e.g., a threading technique used in a surgery), or calculations (e.g., forces required in certain steps or techniques). In embodiments, the output module 742 polls its inputs to receive data describing materials required for certain steps or techniques, or specialists required for the specific steps or techniques.

In step 1706, the output module 742 receives a request from the patient module 720 to send the data stored in the operation database 744. For example, the output module 742 receives a request from the patient module 720 for data such as a patient ID, a type of surgery, or a 3D rendering of the patient's medical images.

In step 1708, the output module 742 sends the data stored in the operation database 744 to the patient module 720. The output module 742 polls its inputs to receive a request from the patient module 720. For example, the output module 742 sends data to the patient module 720 such as a patient ID, a type of surgery, or a phase of the surgery. In step 1710, the output module 742 returns control to the S.R.N. base module 736.

FIG. 18 is a chart illustrating an example database, in accordance with one or more embodiments. The operation database 744 is shown by FIG. 18. In some embodiments, operation database 744 stores information describing a surgical process selected or specified by a user using the CAD GUI 746. The process of user input using the CAD GUI 746 is illustrated and described in more detail with reference to FIG. 16. In embodiments, the operation database 744 stores information describing a patient ID (e.g., JS123), a type of surgery (e.g., EDL tendon repair surgery), or a 3D rendering of a patient's medical images. Likewise, embodiments of the operation database 744 can include different and/or additional components or can be arranged in different ways.

In some embodiments, the operation database 744 stores information describing a phase of the surgery, such as an identification phase, a cutting phase, or a suture phase. In some embodiments, the operation database 744 stores information describing a surgical process, data files (e.g., data files for replays of a surgical step input into the CAD GUI 746), or (x, y, z) coordinates of the patient's anatomy. In some embodiments, the operation database 744 stores information describing surgical tools used, surgical techniques used (e.g., a threading technique used in the surgery), or calculations (e.g., forces required in certain steps or techniques).

In some embodiments, the operation database 744 stores information describing materials required for certain surgical steps or techniques, or specialists required for the specific steps or techniques. For example, a surgical process is divided into an identification phase, a cutting phase, and a suture phase. In the identification phase, the surgical robot 702 uses sensors or an imaging device attached to the end effector 714 to identify a lacerated tendon. In the cutting phase, the surgical robot 702 cuts or cleans the lacerated ends of the tendon to remove frayed ends. In the suture phase, the surgical robot 702 sutures the ends of the lacerated tendon together to repair the tendon.

In embodiments, the system of FIG. 7 performs, using surgical robot 702, a robotic arthroscopic surgical procedure based on an extracted surgical process. For example, one or more end effectors 714 of surgical robot 702 secure a first location of a lacerated tendon and a second location of a lacerated tendon. In an identification phase of the surgical process, the lacerated tendon is identified and secured by a first end effector and a second end effector. A cutting phase can include cutting (by a knife end effector) the frayed end of the first location of the lacerated tendon, and removing the knife end effector. The cutting phase can include releasing the first location of the lacerated tendon, and cutting (by the knife end effector) the frayed end of the second location of the lacerated tendon. The cutting phase can include removing the knife end effector and releasing the second location of the lacerated tendon.

The suture phase can include inserting (by a suture end effector) a suture intertendinous on a fibula side through the lacerated portion of the tendon, exiting (by the suture end effector) through a dorsal surface of the tendon on the fibula side, and passing the suture ventrally to the tendon. The suture phase can include inserting (by the suture end effector) the suture through a dorsal aspect of the tendon on a tibia side, exiting (by the suture end effector) the suture through the lacerated region of the tendon on the tibia side, and repeating the process on the second location of the lacerated tendon. The suture phase can include tying the suture to complete the surgery.

Figures 19, 20:
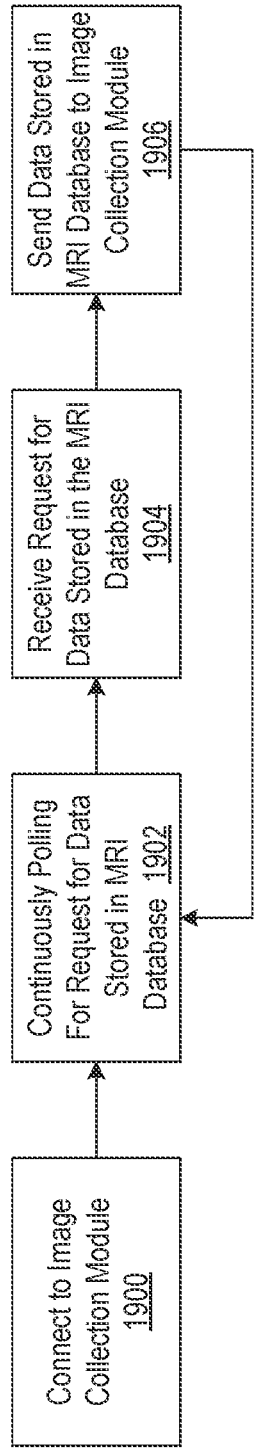
FIG. 19 is a flow diagram illustrating an example process, in accordance with one or more embodiments.
FIG. 20 is a chart illustrating an example database, in accordance with one or more embodiments.

FIG. 19 is a flow diagram illustrating an example process, in accordance with one or more embodiments. An example operating room 102 is illustrated and described in more detail with reference to FIG. 1. In some embodiments, the process of FIG. 19 is performed by the MRI module 750. The MRI module 750 is illustrated and described in more detail with reference to FIG. 7. In other embodiments, the process of FIG. 19 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

In step 1900, the MRI module 750 connects to the image collection module 738. In step 1902, the MRI module 750 polls its inputs to receive a request from the image collection module 738 for data stored in the MRI database 752. For example, the MRI module 750 polls its inputs to receive a request for data describing a patient ID, a first name of a patient, or a last name of a patient. In embodiments, the MRI module 750 polls its inputs to receive a request for data describing an anatomical region for which an MRI was taken (e.g., an ankle). In embodiments, the MRI module 750 polls its inputs to receive a request for data describing data files (e.g., file JS-Ankle #1.JPEG).

In step 1904, the MRI module 750 receives a request from the image collection module 738 for the data stored in the MRI database 752. For example, the MRI module 750 receives a request for a patient ID, a first name of the patient, or data files, such as JS-Ankle #1.J PEG.

In step 1906, the MRI module 750 sends the data stored in the MRI database 752 to the image collection module 738. The MRI module 750 polls its inputs for a request from the image collection module 738 for data stored in the MRI database 752.

FIG. 20 is a chart illustrating an example database, in accordance with one or more embodiments. The MRI database 752 is shown by FIG. 20. In some embodiments, the MRI database 752 stores information describing a patient ID (e.g., JS123), a first name of a patient (e.g., John), or a last name of the patient (e.g., Smith). In some embodiments, the MRI database 752 stores information describing an area in which the MRI was taken (e.g., an ankle) or data files (e.g., file JS-Ankle #1.JPEG). Likewise, embodiments of the MRI database 752 can include different and/or additional components or can be arranged in different ways. In some embodiments, the MRI database 752 stores information describing MRI data of a patient.

Figure 21:
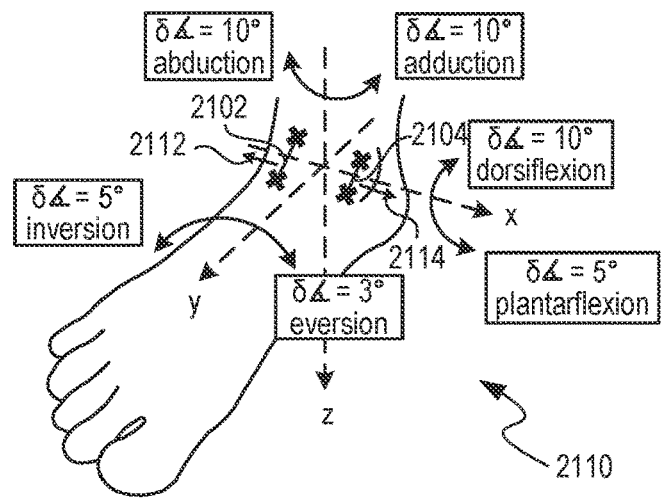
FIG. 21 shows movement of the human ankle, in accordance with one or more embodiments.
Figure 22A:
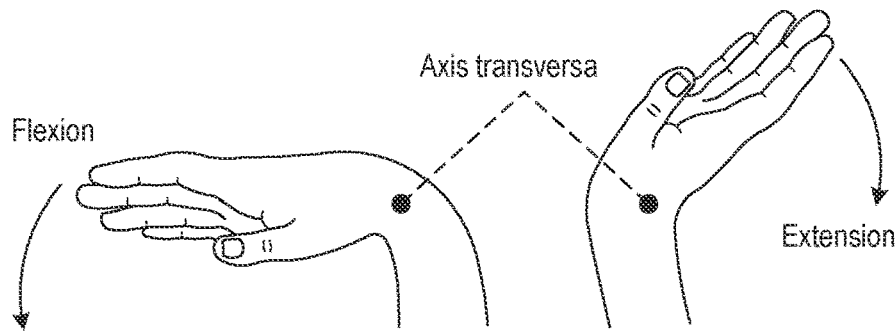
FIGS. 22A and 22B show movement of the human wrist, in accordance with one or more embodiments.
Figure 22B:
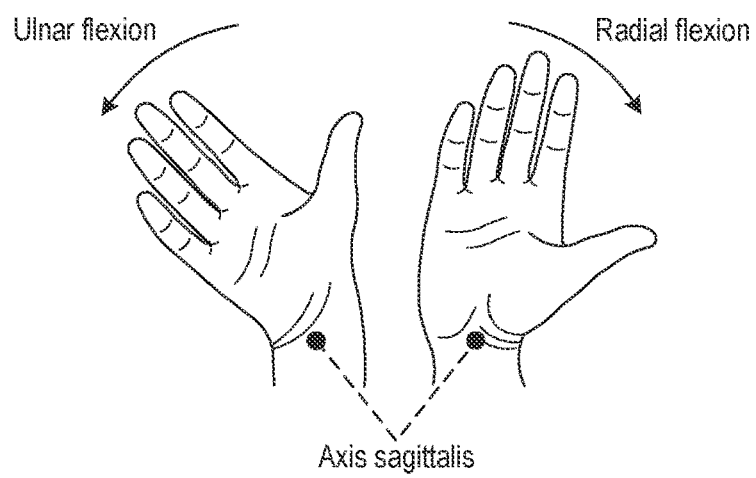

FIG. 21 shows movement of the human ankle, in accordance with one or more embodiments. FIGS. 22A and 22B show movement of the human wrist, in accordance with one or more embodiments. The systems disclosed herein can develop surgical plans to achieve the targeted motion and can simultaneously display pre-operative biomechanics and intraoperative biomechanics, pre-operative renderings of the surgical site and captured images of the surgical site, captured images of the surgical site and metrics, or combinations thereof. This allows a user to evaluate the accuracy of pre-operative predictions, progress of the surgical procedure, and/or real-time monitoring of metrics. For example, a user can input one or more target outcome values, such as the number of degrees of freedom, range of motion, maximum/minimum motion/joint angles, or the like. The system can then perform any number of simulations using one or more virtual models to generate a surgical plan that meets the user inputted target outcome values.

Advantageously, surgical steps can be generated and provided to a surgical system to perform the procedure to meet the predicted outcomes based on soft tissue compliance, joint mechanics, loading, activities performed by patient, etc. The system can then update surgical plans to achieve the target outcome values and/or other user input. The number and position of anchor points, connections, and other features of the tethering can be selected to achieve the outcome criteria. For example, prior to conducting a surgery, the systems disclosed herein can simulate the mobility (e.g., sit, stand, walk, etc.) of the patient after the surgery.

FIG. 21 shows tethering 2102, 2104 (via anchors and sutures) that can stabilize the joint 2110. Virtual connections 2102, 2104 can be used in simulations to generate values or metrics for the ankle. For example, the values can include, for example, angles of abduction, dorsiflexion, plantarflexion, eversion, inversion, and/or other metrics, which can be displayed for evaluating predicted outcomes. The system can move tethering in a virtual model to perform additional simulations. For example, the tethering 1502, 1504 can be moved to another location, as illustrated by arrows 2112, 2114, respectively. The change in biomechanics based on a modification can be illustrated for viewing. For example, the change in the abduction, adduction dorsiflexion, plantarflexion, eversion, and/or inversion can be calculated and displayed.

By way of example, the pre-operative range of motion of the ankle can be, for example, dorsiflexion of 20°-30°, plantarflexion of 40°-50°, inversion/eversion of 30°, supination of 5°, or other ranges of motion. The change in tethering positions can result in an angle change of abduction of about 10° in either direction, angle of dorsiflexion of 10°, plantarflexion angle of 5°, eversion angle of 3°, and/or inversion angle of 5°. Bone-ligament tethering of ankle structures can be selected to achieve one or more of target outcome values. A user can move the location of the tethering to see the effects with joint movement in real-time.

Referring to FIGS. 22A and 22B, bone-ligament tethering, or other surgical steps, can be generated to modify the wrist to achieve one or more of target outcome values. A user can input target outcome values, such as a flexion of 80°-90°, extension of 75°-85°, radial flexion of 20°-22°, ulnar flexion of 35°, or other ranges of motion or values.

Virtual models and simulations disclosed herein can be performed to generate the surgical plans for the Figures herein. 3D images generated can be of the virtual model, simulated virtual steps of the procedure, and other images associated with the model/simulation. In some procedures, the CAD GUI 746 of FIG. 7 receives images of the patient's anatomy and generates virtual two-dimensional or three-dimensional models with surface topologies, tissue properties, boundary conditions, etc. The models can represent anatomical features of interest, including skin, bones, soft tissue, fluids, connective tissue, and ligaments using the embodiments, methods, and features disclosed herein. The embodiments, methods, and features disclosed herein can be used to implement the examples discussed below.

In some virtually simulated leg procedures, an incision is made from a tip of the fibula to the extensor retinaculum of the virtual model. Virtual holes can be drilled in structures, such as the fibula, to place virtual drill guides, anchors, and other features along the anatomy. Multiple positions of fibula anchors can be analyzed to select a target fibula anchor position. One or more sutures can pass through the fibula anchor and be connected to another structure, such as ligaments (e.g., extensor retinaculum). The suture can then be routed back and returned to the anchor. In this manner, the fibula anchor can be used to limit motion of another structure. The system can analyze the characteristics and properties of the extensor retinaculum based on, for example, X-ray images, MRIs, and other patient images. Ankle simulations can be performed to, for example, select the number and locations of the anchors and sutures extending through, under, and/or above the extensor retinaculum.

Anchoring of the extensor retinaculum can cause tendons of the extensor muscles to be pulled inwardly toward the fibula. This can cause tensioning of the tendons of the peroneus tertius and the extensor digitorum longus. The alterations to the tendons can be virtually simulated based on the virtual tensioning of the sutures. This allows for virtual simulations of movement of a joint under loading, performing pre-defined determined tasks, etc. The tensioning of the extensor retinaculum can be increased or decreased to increase or decrease, respectively, the tensioning of the underlying tendons. Three-dimensional modeling analyses can be performed to accurately determine procedures to be performed based on the tensioning. In some procedures, additional or ancillary procedures can be performed to further adjust the procedure.

Additional anchors can be positioned along the leg. By way of example, a calcaneus anchor can be attached to the calcaneus bone. One or more sutures can be connected to the calcaneus anchor and connected to the extensor retinaculum (e.g., superior extensor retinaculum, inferior extensor retinaculum, etc.) one or more times in, for example, a weaving fashion, an overlapping fashion, or the like. The suture can then be attached to the fibula anchor, the calcaneus anchor, or another anchor. Tensioning of the extensor retinaculum can alter underlying tissue by, for example, tensioning one or more of the longus tendons. The number of anchors, number of times the suture passes through or is connected to the ligament, and other parameters can be selected based on the targeted outcome. Advantageously, overall motion of the joint can be analyzed based on multiple connections between multiple anatomical structures of the joint or structures surrounding the joint. The output from the simulations can be displayed for movements of the anatomy as illustrated in FIGS. 21-22B. A user can modify, adjust, and/or input values for the patient databases to perform additional simulations to generate predicted outcomes and confidence scores.

Inter-operative data can be compared to the predicted data in the patient databases. If differences between the predicted data and the actual data exceed a threshold, one or more warnings can be sent to the user or the robotic system. The surgical procedure can be adjusted to compensate for the changes. In some embodiments, the user can stop the procedure to perform alternative steps or evaluation based on the alert. The thresholds for alerts can be selected using machine learning models trained based on previous procedures. This allows alerts to be accurately generated.

The virtual robotic surgical procedures disclosed herein can be performed using simulation and computer-aided design. For example, the virtual robotic surgical procedure is performed using the one or more processors to aid in the creation, modification, analysis, or optimization of implants and tools, and to create a database for manufacturing. Further, the virtual robotic surgical procedure can use vector-based graphics to depict the surgical implants, and can also produce raster graphics showing the overall appearance and path of the surgical implant in the virtual robotic surgical procedure. Moreover, the output of the virtual robotic surgical procedure can convey information, such as processes, dimensions, and tolerances, according to application-specific conventions. The virtual robotic surgical procedure can be used to design curves and figures in two-dimensional space or curves, surfaces, and solids in three-dimensional space, and to rotate and move a virtual model of the surgical implant for viewing. For example, virtual joints can be generated for 2D or 3D spaces.

Simulations for the virtual robotic surgical procedure can be performed using virtual models that can include two- or three-dimensional models to evaluate, for example, one or more steps of a surgical procedure (or entire procedure), predicted events, outcomes, etc. The simulations can be used to identify and assess biomechanics, access paths, stresses, strains, deformation characteristics (e.g., load deformation characteristics, load distributions, etc.), fracture characteristics (e.g., fracture toughness), fatigue life, etc. The virtual model can include a model of the patient's anatomy, implant(s), end effectors, instruments, access tools, or the like. The one or more processors can generate a three-dimensional mesh to analyze models. Machine learning techniques can be used to create an optimized mesh based on a dataset of joints, anatomical features, and implants, or other devices. The three-dimensional models, surfaces, and virtual representations can be generated by CAD software, FEA software, and robotic control software/programs based on patient data (e.g., images, scans, etc.), implant design data, or the like. A user can view, manipulate (e.g., rotate, move, etc.), modify, set parameters (e.g., boundary conditions, properties, etc.), and interact with the models. The control parameters, robotic kinematics, and functionality can be used to generate the simulations. In some embodiments, models of end effectors of a robotic system are generated to perform virtual procedures on virtual anatomical models. Virtual simulations of surgical procedures in which a user selected robotic surgical steps and physician steps can be used to generate, modify, and select surgical plans, surgical robot configurations, or the like.

Pre-operative simulations can be performed for different surgical robots using pre-operative patient data (e.g., pre-operative scans, images, etc.). A surgical robot for performing a surgical procedure or portion thereof can be selected based on the simulation(s). This allows a healthcare provider to select a surgical robot suitable for a particular procedure. Additionally, the simulations can be used to generate, modify, and/or verify surgical plans. In some embodiments, a configuration of the surgical robot is selected based on the simulations. For example, multiple simulations can be performed for a surgical robot in different configurations (e.g., the surgical robot having different end effectors) and using different surgical techniques. The healthcare provider can select the surgical robot configuration and surgical plan based, at least in part, on the simulations. End effectors and tools of the surgical robot, imaging equipment, and manual equipment can be selected based on the simulations.

In some embodiments, the surgical system can perform virtual simulations based on one more design parameters, including simulation time, resource usage, accuracy level, and/or data output. The simulation time can be selected so that the virtual simulation is completed within a time period (e.g., percentage of completion time for a surgical step, percentage of surgical procedure duration, user-input time period, etc.). The complexity of the models can be increased or decreased to decrease or increase, respectively, the simulation time period. If the user requests a significant amount of data output (e.g., joint mechanics, loads applied to anatomical structures, multiple implants, fatigue life, etc.), high complexity models (e.g., FEA models with a large number of elements/nodes, optimization models, fluid flow models, etc.) can be generated. Resource usage parameters can be used to select features of three-dimensional models of the anatomy and implants based on available processing resources, including central processing unit (CPU) cycles, memory space, network bandwidth, or a combination thereof. For example, the resource usage parameters can be set to limit usage of such processing resource(s). The surgical system can perform one or more corrective measures to free up the amount of resources required to enable process resources to be available to the robotic apparatus to complete tasks. The corrective measures can include one or more of allocating memory space, prioritizing packets, limiting CPU usage, and/or throttling bandwidth (e.g., throttling network bandwidth). The complexity and features (e.g., surface contours, feature matching, etc.) can be selected based on the available computing resources.

The surgical system can determine the simulation time period based on an action schedule of the surgical plan, a time allocated for the at least one robotic surgical action to be planned and completed, etc. The virtual simulations can be performed while one or more instruments are at least partially positioned within a patient to complete a current surgical action. This allows simulations to be performed concurrently with surgical actions on the patient. Suturing tools, anchoring tools, bronchoscopes, endoscopes, and/or imaging equipment are at least partially positioned within the patient to obtain the intraoperative patient data.

Virtual surgical procedures can include one or more robotic assisted surgical steps, automated surgical steps, and/or physician-controlled surgical steps. Intraoperative virtual simulations can be performed at any time during a surgical procedure to plan future surgical steps or actions. The system can collect real-time surgical data, patient data, or other information continuously or periodically before, after, and/or during surgical steps. Surgical plans can be modified based on intraoperative planning, trained machine learning models, virtual simulations, etc., and obtained data, such as pre-operative data, intraoperative data (e.g., surgical robot data, patient data, etc.), and/or other data. In some embodiments, virtual simulations are performed based on intraoperative patient data. The virtual simulations can be used to generate one or more robotic surgical actions for an intraoperative surgical plan using a trained machine learning model. The surgical system can control a robotic surgical apparatus to perform the robotic surgical action according to the intraoperative surgical plan. Planned robotic surgical actions can be generated any number of times to dynamically modify the intraoperative surgical plan. The real-time planning enables one or more trained machine learning models to determine surgical steps based on the current status of the patient, functionality of the surgical robotic apparatus, etc. If the surgical robotic apparatus is not configured for performing surgical action(s), a user can be notified that the configuration of the surgical robotic apparatus should be modified by, for example, changing end effectors, installing new instruments, etc. Once reconfigured, the surgical robotic apparatus can continue in autonomous mode, semi-autonomous mode, or another mode.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A surgical robot comprising:
a non-transitory computer-readable storage medium storing computer instructions, which when executed by one or more computer processors cause the surgical robot to:
extract information describing an arthroscopic surgical procedure from a surgical database performing the arthroscopic surgical procedure by the surgical robot;
identify injured soft tissue within an anatomy of a patient using images of the anatomy obtained using an imaging sensor of the surgical robot; and
perform the arthroscopic surgical procedure based on the information, wherein the computer instructions cause the surgical robot to:
secure, by one or more end effectors of the surgical robot, the injured soft tissue; and
suture, by the one or more end effectors, the injured locations to repair the injured soft tissue.

2. The surgical robot of claim 1, wherein the one or more end effectors comprise at least one material that absorbs X-rays, reflects X-rays, or is transparent to X-rays to facilitate visibility of the one or more end effectors when viewed using angiography or fluoroscopy.

3. The surgical robot of claim 1, wherein the surgical robot comprises a mechanically actuated robotic arm or lever having at least two degrees of freedom.

4. The surgical robot of claim 3, wherein the robotic arm comprises the one or more end effectors or the imaging sensor.

5. The surgical robot of claim 1, wherein the imaging sensor is integrated into a catheter assembly.

6. The surgical robot of claim 1, wherein sensor data acquired by the imaging sensor is used to train a machine learning model for generating the information.

7. The surgical robot of claim 1, wherein the imaging sensor comprises an X-ray dosimeter configured to monitor an intensity of X-rays emitted toward the patient to prevent a dose of radiation from exceeding a threshold.

8. The surgical robot of claim 7, wherein the surgical robot is configured to prevent the dose of radiation from exceeding the threshold based on monitoring the intensity of X-rays emitted toward the patient by reducing the intensity of the X-rays.

9. The surgical robot of claim 7, wherein the surgical robot is configured to prevent the dose of radiation from exceeding the threshold based on monitoring the intensity of X-rays emitted toward the patient by reducing a duration in which the X-rays are emitted toward the patient.

* * * * *